(12) United States Patent
Moshelion et al.

(10) Patent No.: US 10,897,849 B2
(45) Date of Patent: Jan. 26, 2021

(54) CHARACTERIZATION OF PLANT BEHAVIOR USING TRANSPIRATION RATE AND WATER UPTAKE RATE

(71) Applicant: Yissum Research Development Company of the Hebrew University of Jerusalem Ltd., Jerusalem (IL)

(72) Inventors: Menachem Moshelion, Rechovot (IL); Rony Wallach, Karmei Yosef (IL); Ofer Halperin, Kibbutz Mishmar HaSharon (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 711 days.

(21) Appl. No.: 15/307,028

(22) PCT Filed: Apr. 28, 2015

(86) PCT No.: PCT/IL2015/050443
§ 371 (c)(1),
(2) Date: Oct. 27, 2016

(87) PCT Pub. No.: WO2015/166493
PCT Pub. Date: Nov. 5, 2015

(65) Prior Publication Data
US 2017/0042098 A1 Feb. 16, 2017

Related U.S. Application Data

(60) Provisional application No. 61/985,308, filed on Apr. 28, 2014.

(51) Int. Cl.
*A01G 7/00* (2006.01)
*G01N 33/00* (2006.01)
*G06Q 50/02* (2012.01)

(52) U.S. Cl.
CPC ........... *A01G 7/00* (2013.01); *G01N 33/0098* (2013.01); *G06Q 50/02* (2013.01)

(58) Field of Classification Search
None
See application file for complete search history.

(56) References Cited

FOREIGN PATENT DOCUMENTS

| CN | 102550310 | 7/2012 | | |
|---|---|---|---|---|
| CN | 1030636555 | 4/2013 | | |
| JP | 2011-120557 | 6/2011 | | |
| JP | 2011120557 A | * | 6/2011 | |
| KR | 2013-0074948 | 7/2013 | | |
| KR | 20130074948 A | * | 7/2013 | |
| WO | WO-2007023204 A1 | * | 3/2007 | ............. G01N 27/06 |
| WO | WO 2011/162220 | 12/2011 | | |
| WO | WO 2012/101546 | 8/2012 | | |
| WO | WO-2012101546 A1 | * | 8/2012 | ............... A01G 7/00 |
| WO | WO 2007/023204 | 3/2015 | | |
| WO | WO 2015/166493 | 11/2015 | | |

OTHER PUBLICATIONS

Van Leperen, W., and H. Madery. "A new method to measure plant water uptake and transpiration simultaneously." Journal of experimental botany 45.1 (1994): 51-60.*
KR20130074948A with English translation from Google Patents downloaded Sep. 4, 2020 (Year: 2013).*
JP2011120557A with English translation from Google Patents downloaded Sep. 4, 2020 (Year: 2011).*
Harris, Donald G. "Automated Precision Balance System for Measuring Transpiration from Large Individual Plants 1." Agronomy Journal 62.1 (1970): 71-74. (Year: 1970).*
Granier, Christine, et al. "PHENOPSIS, an automated platform for reproducible phenotyping of plant responses to soil water deficit in *Arabidopsis thaliana* permitted the identification of an accession with low sensitivity to soil water deficit." New Phytologist 169.3 (2006): 623-635. (Year: 2006).*
International Preliminary Report on Patentability dated Nov. 10, 2016 From the International Bureau of WIPO Re. Application No. PCT/IL2015/050443.
International Search Report and the Written Opinion dated Nov. 4, 2015 From the International Searching Authority Re. Application No. PCT/IL2015/050443.
Communication Pursuant to Article 94(3) EPC dated Jan. 24, 2018 From the European Patent Office Re. Application No. 15753776.2. (6 Pages).
Notification of Office Action and Search Report dated Dec. 24, 2018 From The State Intellectual Property Office of the People's Republic of China Re. Application No. 201580034237.4 and Its Translation Into English. (22 Pages).
Notification of Office Action dated Sep. 23, 2019 From the National Intellectual Property Administration of the People's Republic of China Re. Application No. 201580034237.4 and Its Translation Into English. (14 Pages).
Office Action dated Jul. 15, 2020 From the Israel Patent Office Re. Application No. 248582 and its Translation Into English. (6 Pages).

\* cited by examiner

*Primary Examiner* — G Steven Vanni

(57) ABSTRACT

A system for characterizing a plant is disclosed. The system comprises: a plurality of sensors configured to sense a first parameter indicative of a transpiration rate from the whole plant and a second parameter indicative of a water uptake rate into the whole plant. The system also comprises a processor configured to receive signals from the sensors, to process the signals to calculate both the parameters, and to characterize the plant according to the calculated parameters. In some embodiments of the present invention the processor is configured for calculating at least one of the first parameter and the second parameters momentarily.

19 Claims, 24 Drawing Sheets
Specification includes a Sequence Listing.

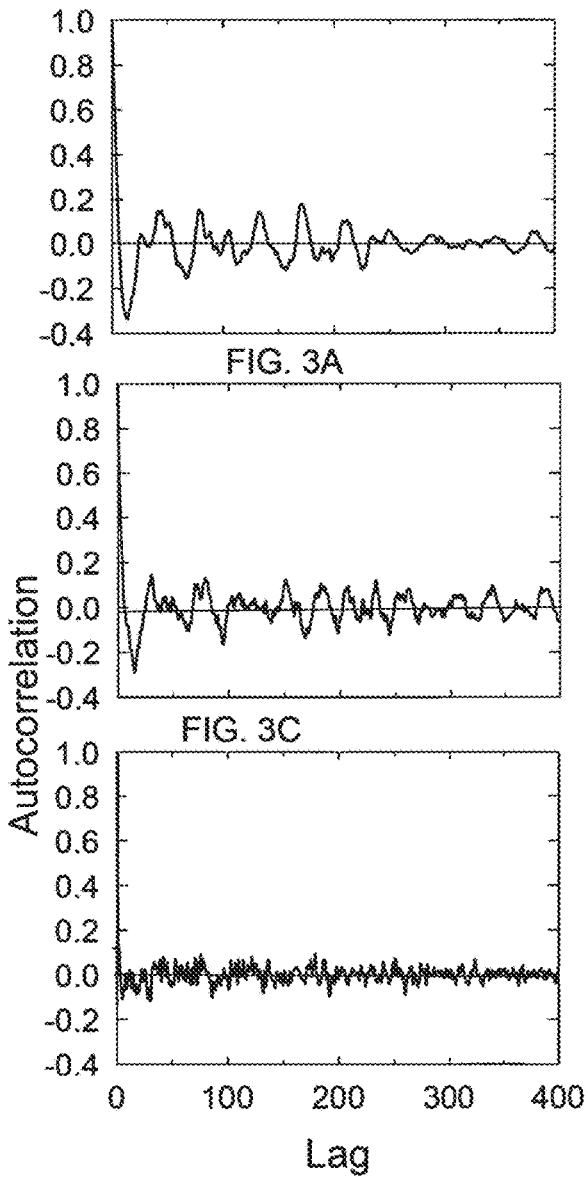
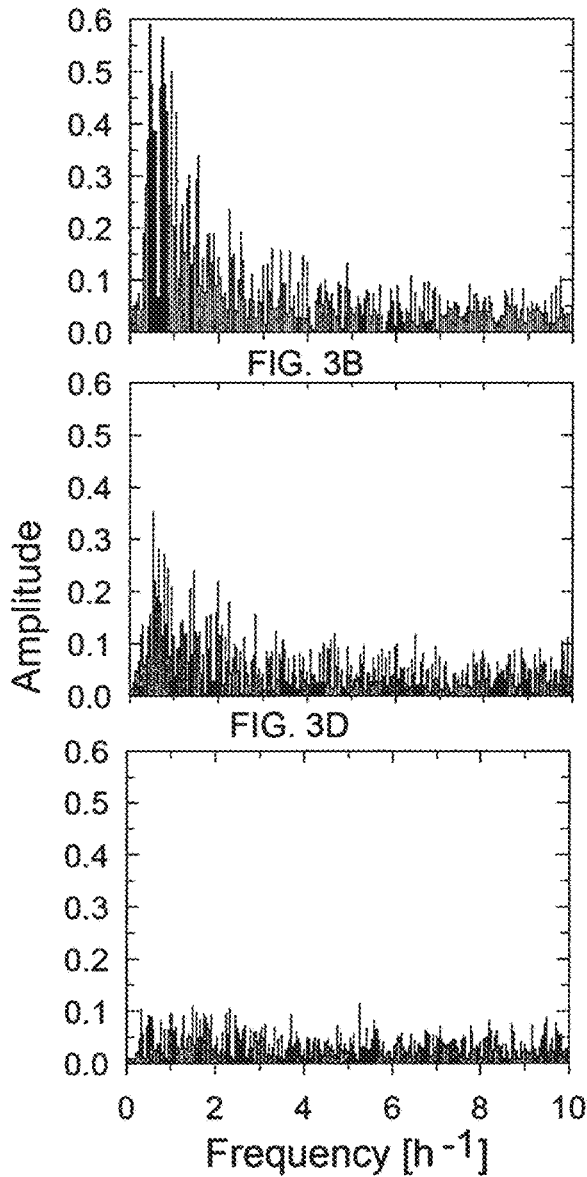
FIG. 3A
FIG. 3B
FIG. 3C
FIG. 3D
FIG. 3E
FIG. 3F

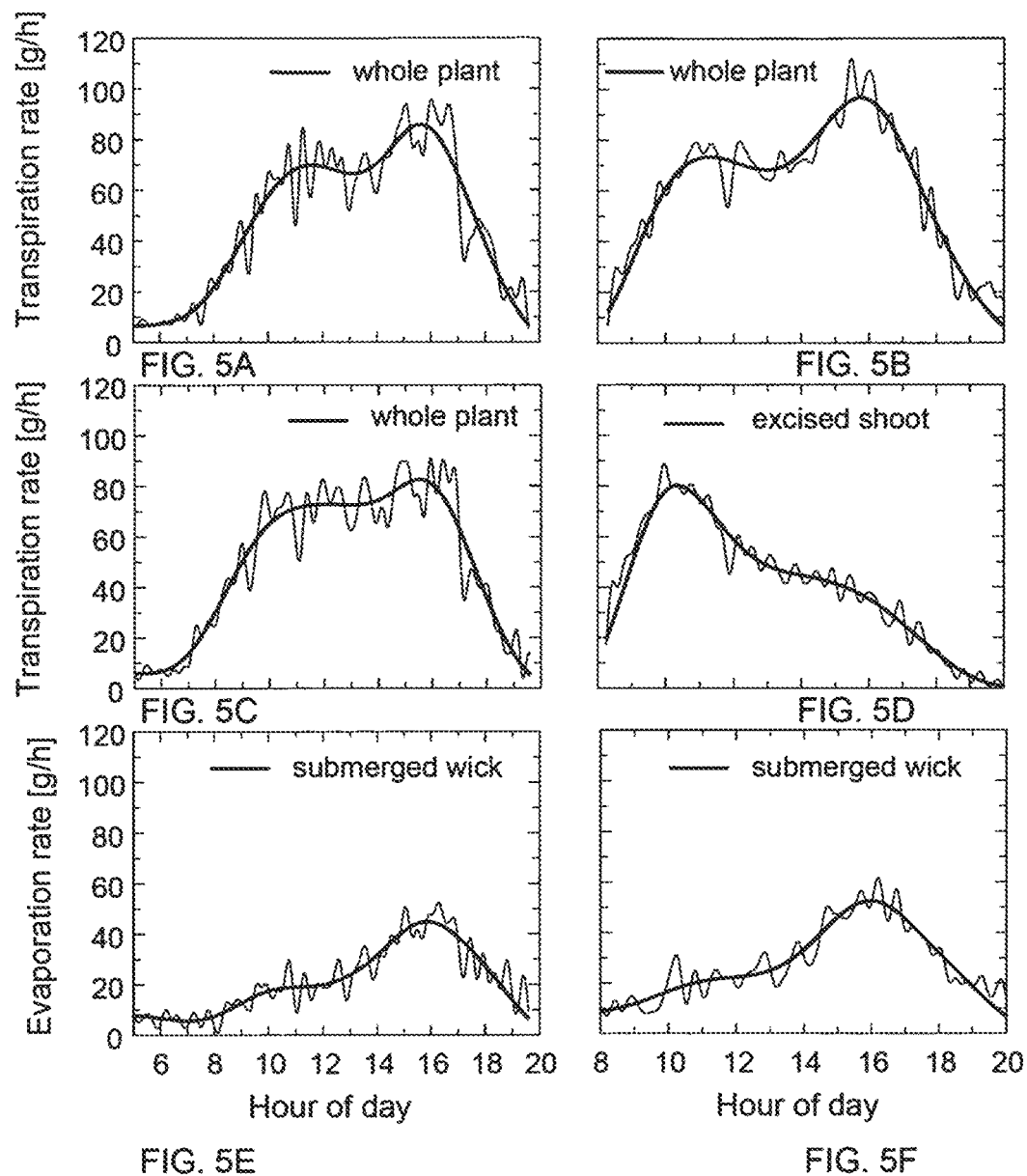

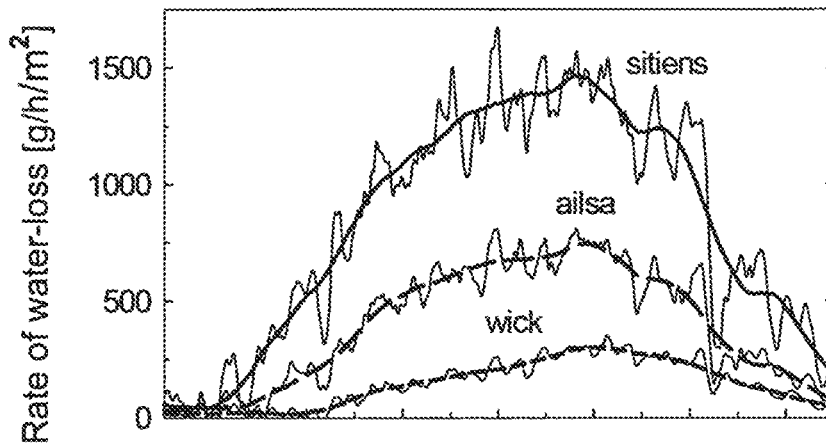
FIG. 6A
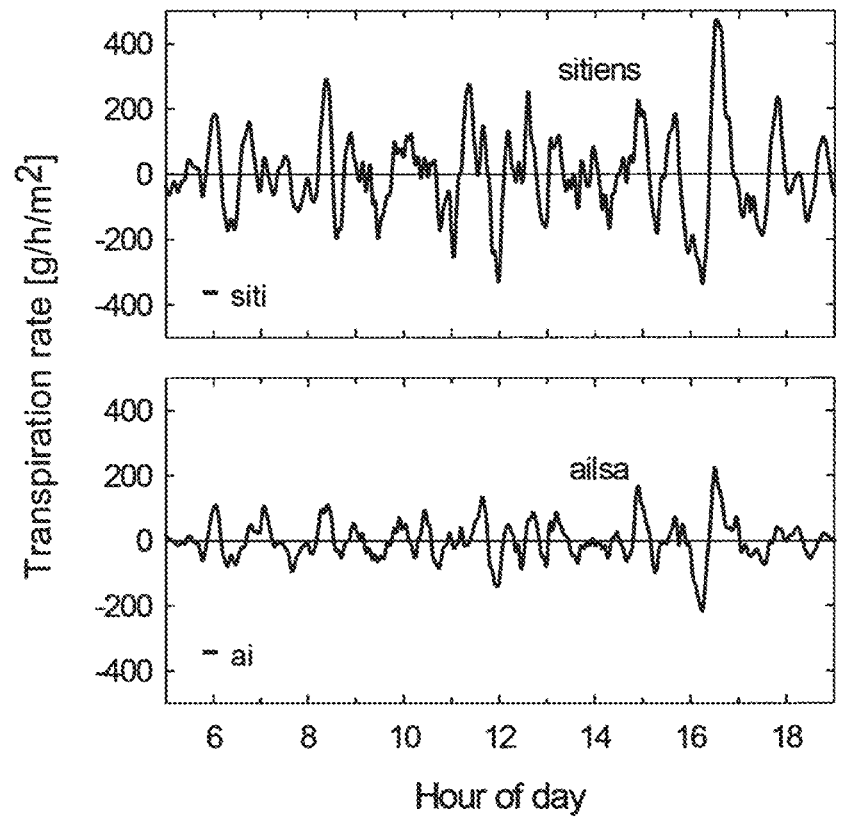
FIG. 6B
FIG. 6C

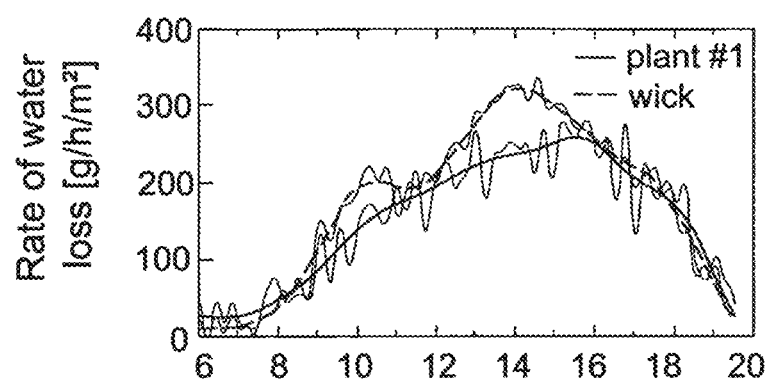
FIG. 7A
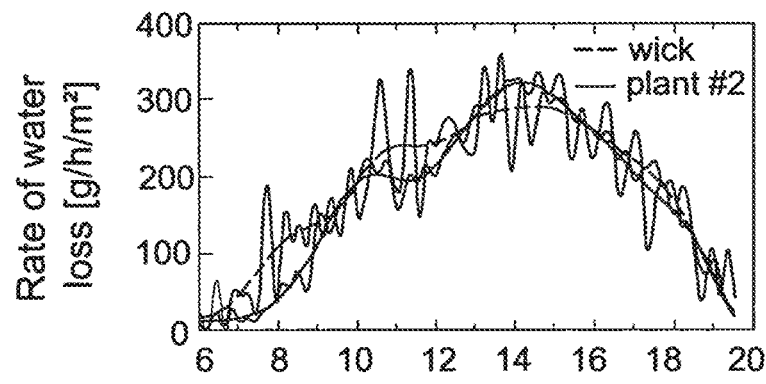
FIG. 7B
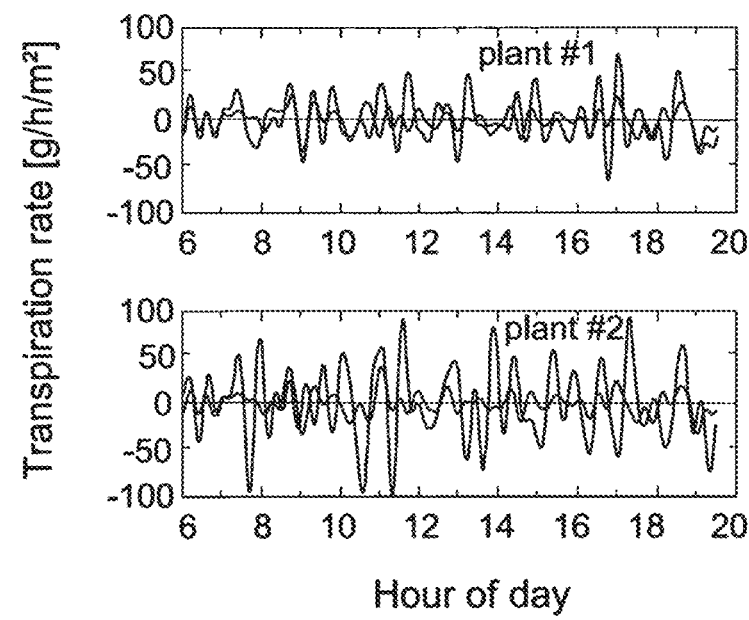
FIG. 7C
FIG. 7D

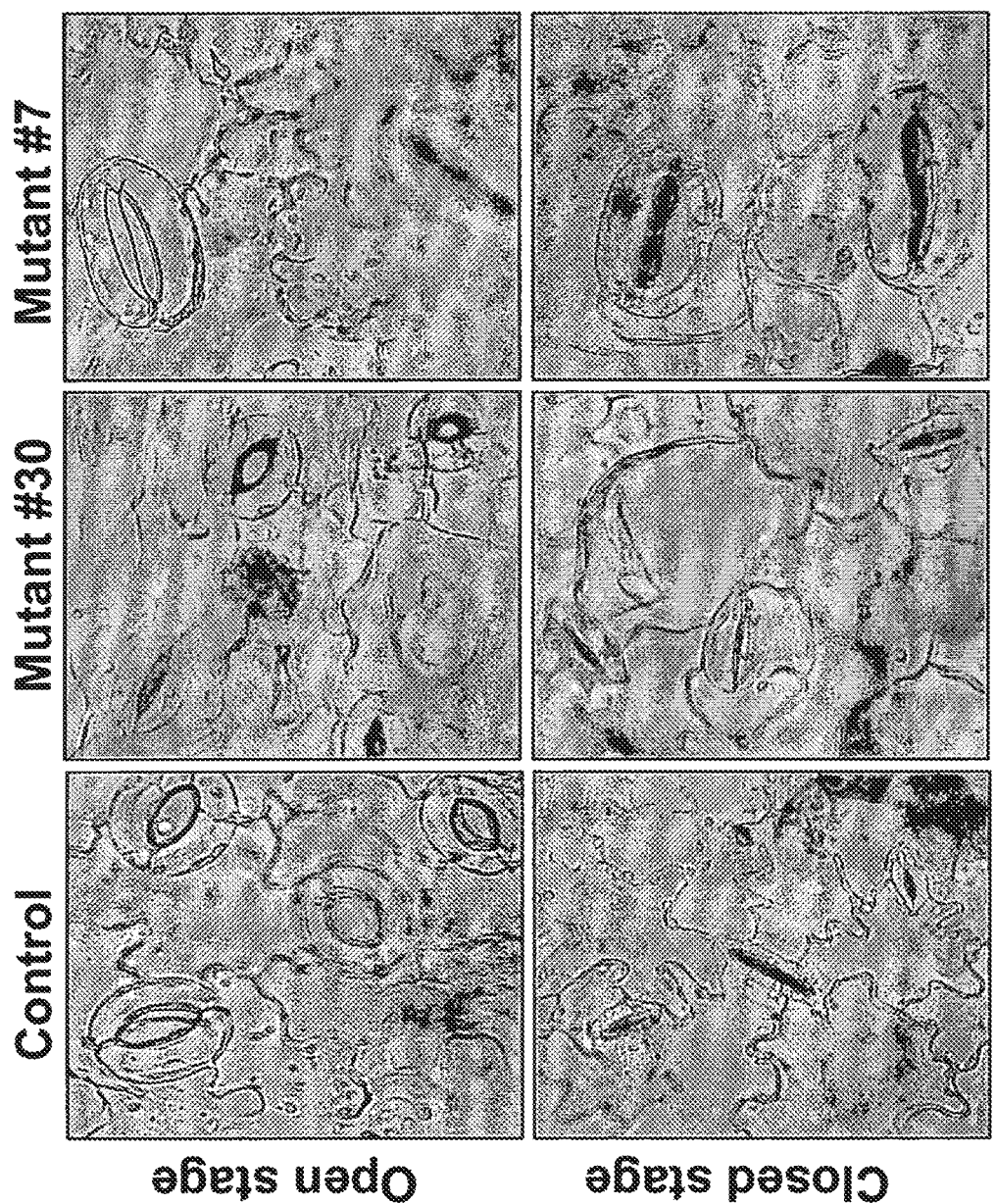

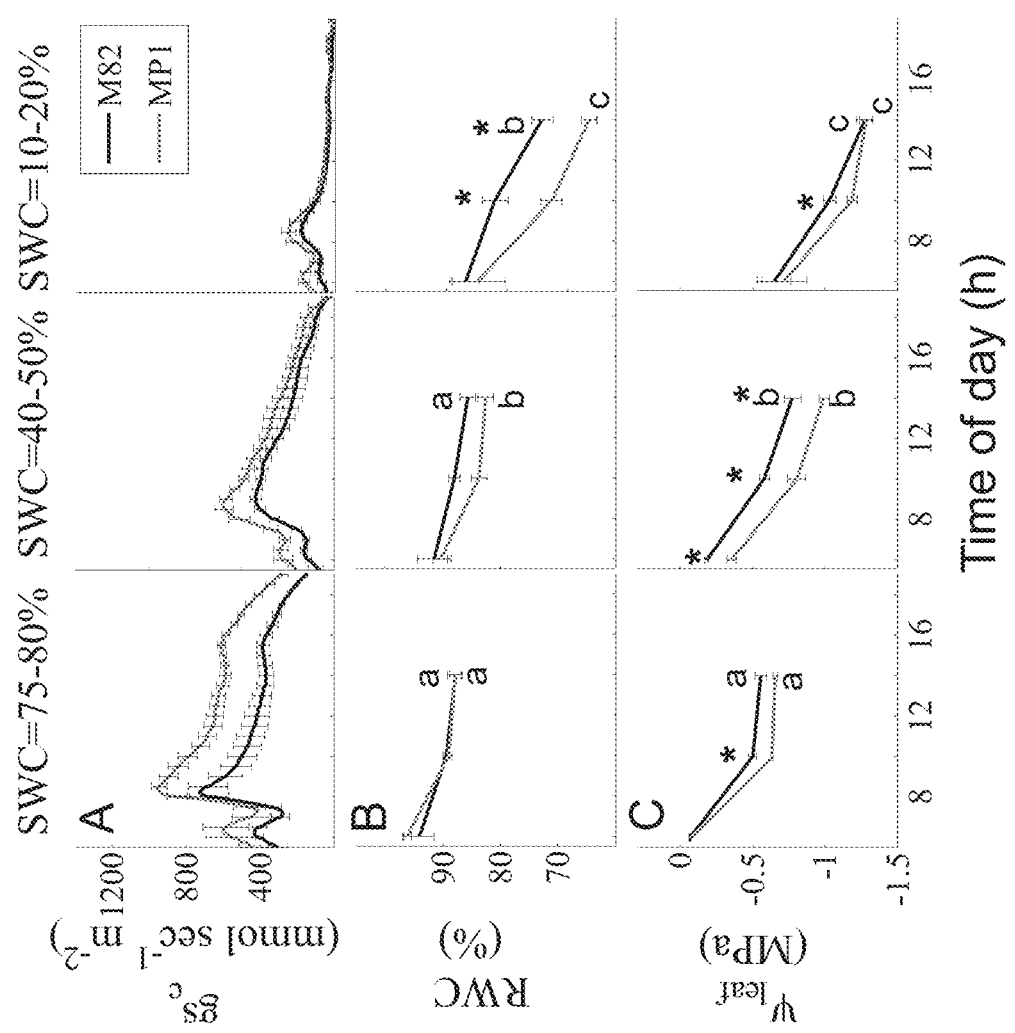

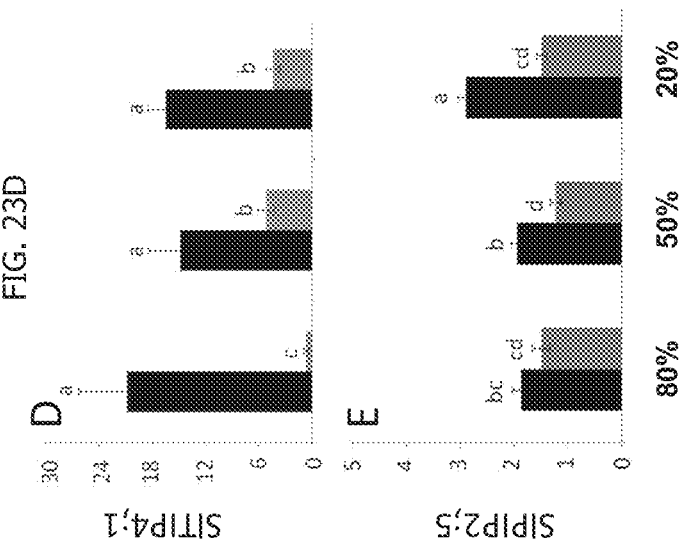
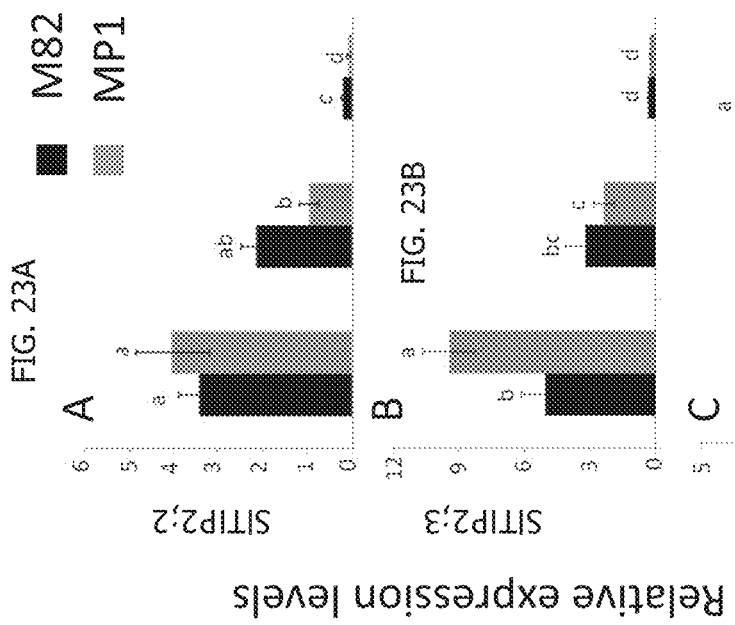
FIG. 23A, FIG. 23B, FIG. 23C, FIG. 23D, FIG. 23E

US 10,897,849 B2

CHARACTERIZATION OF PLANT BEHAVIOR USING TRANSPIRATION RATE AND WATER UPTAKE RATE

RELATED APPLICATIONS

This application is a National Phase of PCT Patent Application No. PCT/IL2015/050443 having International filing date of Apr. 28, 2015, which claims the benefit of priority under 35 USC § 119(e) of U.S. Provisional Patent Application No. 61/985,308 filed on Apr. 28, 2014. The contents of the above applications are all incorporated by reference as if fully set forth herein in their entirety.

SEQUENCE LISTING STATEMENT

The ASCII file, entitled 67868SequenceListing.txt, created on Oct. 28, 2020, comprising 4,152 bytes is incorporated herein by reference.

FIELD AND BACKGROUND OF THE INVENTION

The present invention, in some embodiments thereof, relates to agriculture and, more particularly, but not exclusively, to a method and system for characterizing plant behavior.

Worldwide development production of new abiotic-stress-resistant cultivars, i.e., those resistant to such stress conditions as drought, extreme temperatures, or salinity, is on the rise, owing to the expansion of agriculture into previously uncultivated areas. Such areas often suffer from low soil fertility, groundwater of variable salinity, sensitivity to water-logging, deterioration of irrigation-water quality, and irrigation with marginal water with high chloride concentrations. The threat of global warming and the associated fluctuations in weather conditions and precipitation levels are expected to accelerate the expansion of agriculture into previously uncultivated areas.

A major and immediate response of many plant species to abiotic stresses is a decrease in growth rate, which eventually leads to a significant decrease in yield. Among the reasons for the reduction in growth rate under abiotic stresses is a decrease in root conductivity, which induces abrupt stomatal closure, leading to decreased rates of transpiration and photosynthesis. Plants are able to cope with abiotic stresses using a variety of stress-defense mechanisms, such as osmotic regulation, antioxidant protection and ion-homeostasis mechanisms, among others. These mechanisms enable plants to complete their life cycle while maintaining some level of yield, even under stress conditions.

Two main approaches have been to cope with theses problem by producing new stress-resistant cultivars. The first is genetic engineering, using various candidate genes, and the second is classical breeding. However, assessing a plants yield under stress conditions is difficult under field conditions because of the spatial variability of the soil texture, moisture content, and salinity in the field, salinity, and varying light intensity.

WO2010/049939 by the same inventors of this application concerns system and method for identifying one or more plants in a population of two or more plants. The method comprises monitoring one or more parameters of a plant of the population and generating one or more time signals indicative of values of the one or more parameters. The signals are processed to calculate one or both of a transpiration rate of each plant and a rate of change of a transpiration rate over each of one or more time intervals. The plants are then ranked using an algorithm involving the calculated transpiration rates, and plants having a ranking above a predetermined ranking are identified.

SUMMARY OF THE INVENTION

According to an aspect of some embodiments of the present invention there is provided a system for characterizing a plant. The system comprises: a plurality of sensors configured to sense a first parameter indicative of a transpiration rate from the whole plant and a second parameter indicative of a water uptake rate into the whole plant. The system also comprises a processor configured to receive signals from the sensors, to process the signals to calculate both the parameters, and to characterize the plant according to the calculated parameters. In some embodiments of the present invention the processor is configured for calculating at least one of the first parameter and the second parameters momentarily. According to some embodiments of the invention the processor is configured for calculating both the first parameter and the second parameters momentarily.

According to some embodiments of the invention the processor is configured to calculate a score based on the calculated parameters.

According to some embodiments of the invention the plant is a member of a population of plants, and the processor is configured to calculate the score for each plant in the population, and to rank the plants of the population based on the score.

According to some embodiments of the invention the sensors comprise a soil water content sensor for sensing the second parameter and a weight sensor for sensing the first parameter.

According to some embodiments of the invention the system comprises a container containing soil and water and being constituted to receive the plant, wherein the weight sensor is a load cell arranged to sense a weight or a change of weight of the container and contents thereof.

According to some embodiments of the invention the container is covered to reduce or prevent evaporation of the water from the container.

According to some embodiments of the invention the processor is configured to calculate the transpiration rate momentarily from a time-dependent signal generated by the load cell, thereby to provide a time-dependence of the transpiration rate.

According to some embodiments of the invention the processor is configured to calculate a rate of change of the transpiration rate based on the time-dependence of the transpiration rate.

According to some embodiments of the invention the processor is configured to calculate the water uptake rate momentarily from a time-dependent signal generated by the soil water content sensor, thereby to provide a time-dependence of the water uptake rate.

According to some embodiments of the invention the processor is configured to calculate a rate of change of the water uptake rate from the time-dependence of the water uptake rate.

According to some embodiments of the invention the processor is configured to calculate a water usage efficiency of the plant.

According to some embodiments of the invention the system comprises a device configured for measuring an additional parameter indicative of atmospheric demand for water, wherein the processor is configured to receive a time-dependent signal from the device, and calculate the additional parameter, and to calculate a ratio between the first parameter and the additional parameter.

According to some embodiments of the invention the processor is configured to calculate the transpiration rate and to normalize the calculated transpiration rate to at least one normalizing quantity selected from the group consisting of a surface area of the leaves of the plant, a density of stomata in the leaves and amount of soil water.

According to some embodiments of the invention the processor is configured to classify the plant into at least one classification group.

According to some embodiments of the invention the processor is configured to classify the plant into a classification group which is one of: (i) a classification group of plants exhibiting isohydric behavior, and (ii) a classification group of plants exhibiting anisohydric behavior.

According to some embodiments of the invention the processor is configured to calculate variability in leaf relative water content, and wherein the classification is according to the variability.

According to some embodiments of the invention the processor is configured to calculate a shoot weight ratio and a root uptake rate and wherein the variability is calculated based on a difference between the shoot weight ratio and the root uptake rate.

According to some embodiments of the invention the processor is configured to receive expression profiles of at least one aquaporin and wherein the classification is based, in part, on the received expression profile.

According to some embodiments of the invention the processor is configured to estimate a whole plant hydraulic conductivity based on at least one of the parameters, and wherein the classification is based, at least in part on the plant hydraulic conductivity.

According to an aspect of some embodiments of the present invention there is provided a method of characterizing a plant. The method comprises: receiving from a plurality of sensors signals pertaining to a first parameter indicative of a transpiration rate from the whole plant and a second parameter indicative of a water uptake rate into the whole plant. The method further comprises processing the signals to calculate both the parameters, and to characterize the plant according to the calculated parameters. In some embodiments of the present invention at least one of the first parameter and the second parameters is calculated momentarily. In some embodiments of the present invention both the first parameter and the second parameters are calculated momentarily.

According to some embodiments of the invention the method comprises calculating a score based on the calculated parameters.

According to some embodiments of the invention the method comprises controllably varying an ambient condition to which the plant is exposed, and recalculating the score following the variation.

According to some embodiments of the invention the method comprises selecting a range of ambient condition for which the calculated score is above a predetermined threshold.

According to some embodiments of the invention the plant is a member of a population of plants, and the method comprises calculating the score for each plant in the population, and ranking the plants of the population based on the score.

According to some embodiments of the invention the method comprises selecting an ambient condition to which the population of plants is exposed, wherein the ranking is associated with the selected ambient condition.

According to some embodiments of the invention the calculation comprises calculating the transpiration rate momentarily from a time-dependent signal generated by the load cell, thereby providing a time-dependence of the transpiration rate.

According to some embodiments of the invention the method comprises calculating a rate of change of the transpiration rate based on the time-dependence of the transpiration rate.

According to some embodiments of the invention the calculation comprises calculating the water uptake rate momentarily from a time-dependent signal generated by the soil water content sensor, thereby providing a time-dependence of the water uptake rate.

According to some embodiments of the invention the method comprises calculating a rate of change of the water uptake rate from the time-dependence of the water uptake rate.

According to some embodiments of the invention the method comprises calculating a water usage efficiency of the plant.

According to some embodiments of the invention the method comprises receiving a time-dependent pertaining to an additional parameter indicative of atmospheric demand for water, wherein the method comprises calculating the additional parameter and a ratio between the first parameter and the additional parameter.

According to some embodiments of the invention the method comprises normalizing the calculated transpiration rate to at least one normalizing quantity selected from the group consisting of a surface area of the leaves of the plant, a density of stomata in the leaves and amount of soil water.

According to some embodiments of the invention the method comprises classifying the plant into at least one classification group.

According to some embodiments of the invention the method comprises classifying the plant into a classification group which is one of: (i) a classification group of plants exhibiting isohydric behavior, and (ii) a classification group of plants exhibiting anisohydric behavior.

According to some embodiments of the invention the method comprises calculating variability in leaf relative water content, wherein the classification is according to the variability.

According to some embodiments of the invention the method comprises calculating a shoot weight ratio and a root uptake rate, wherein the variability is calculated based on a difference between the shoot weight ratio and the root uptake rate.

According to some embodiments of the invention the method comprises estimating a whole plant hydraulic conductivity based on at least one of the parameters, and wherein the classification is based, at least in part on the plant hydraulic conductivity.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system.

In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-C show the autocorrelation functions for the graphs of FIGS. 2A, 2B, and 2C, respectively;

FIGS. 3B-F show the spectra for a whole-plant, a submerged wick, and constant-weight residual time series, respectively;

FIGS. 5A-F show the smoothed WPT rate and the superimposed oscillations for a typical tomato whole plant, excised shoot, and evaporation rate and the superimposed oscillations for the wet wick;

FIGS. 6A-C show representative results of oscillatory and smoothed WPT rate for an ABA-deficient sitiens plant and a control plant and evaporation rate and the superimposed oscillations for the wet wick;

FIGS. 7A-D show representative results of oscillatory and smoothed WPT rate for two poplar (*Populus alba*) plants and the evaporation rate and superimposed oscillations for the wet wick;

FIG. 10 shows stomata pore size in the control plant and mutant plant of FIGS. 8A and 8B;

FIGS. 15A-C show variation in $gs_c$, leaf RWC and $\Psi_{leaf}$ at different SWC levels. Plants were grown in the lysimeter system and (A) mean (±SE, n=5) and whole plant $gs_c$ were monitored continuously. When the pots reached a predefined high SWC level (70-80%), a moderate SWC level (40-50%, around $\theta_{cr}$ for the summer experiment) and a low SWC level (10-20%), leaves were harvested from the plants in those pots and (B) RWC and (C) $\Psi_{leaf}$ were measured. Each data point is the mean±SE of 5 leaves from 5 different plants from pots that had reached the exact SWC at the time of the measurement (same plants described in FIGS. 13A-E). Asterisks indicate a significant difference (Student's t-test, p<0.05) between the lines within a treatment. Different letters represent significant differences [one-way analysis of variance (ANOVA) test, P<0.05] between midday measurements of the same line in the different treatments.

FIGS. 23A-E show relative expression profiles of SlTIP2;2 SlTIP2;3, SlTIP3;1, SlTIP4;1 and SlPIP2;5 AQPs in M82 and MP1 plants at the different SWC levels. qPCR analysis of the relative expression of (A) SlTIP2;2, (B) SlTIP2;3, (C) SlTIP3;1, (D) SlTIP4;1 and (E) SlPIP2;5 in MP1 (gray bar) and M82 (black bar) at different SWC levels (~80%, ~50%, ~20%). Data are presented as means±SE (N=5). Different letters above the columns represent significant differences (t-test, P<0.05).

DESCRIPTION OF SPECIFIC EMBODIMENTS OF THE INVENTION

Figure 1A:
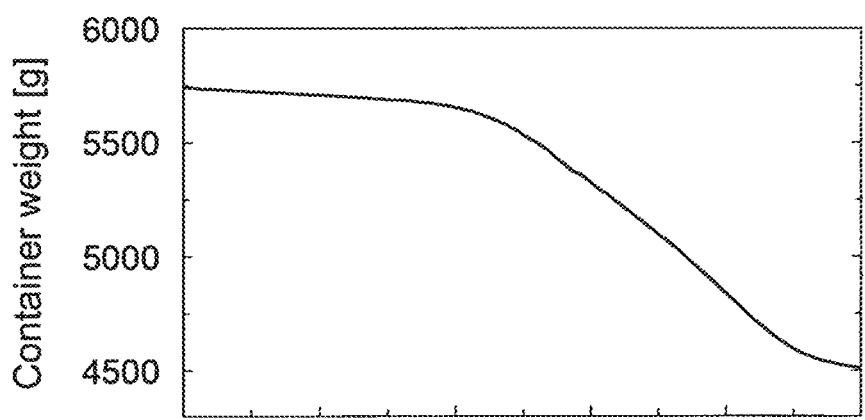
FIG. 1A shows weight variation of a control tomato plant grown in a temperature controlled greenhouse due to transpiration during the night and subsequent day hours.

The present invention, in some embodiments thereof, relates to agriculture and, more particularly, but not exclusively, to a method and system for characterizing a plant.

The present embodiments are based on the realization that to correctly assess plant parameters, it is advantageous in addition to determining the water flux from the whole plant to the atmosphere (by calculating transpiration rate related parameters) also to know the water influx into the whole plant, for example by measuring the soil moister, particularly, but not necessarily at the vicinity of the plant roots. In various exemplary embodiments of the invention at least one, more preferably both, a parameter indicative of transpiration rate and a parameter indicative of water influx is calculated momentarily, for example, at least once every 60 minutes or at least once every 30 minutes or at least once every 10 minutes or at least once every 5 minutes or at least once every 4 minutes or at least once every 3 minutes or at least once every 2 minutes or at least once every 1 minutes.

As used herein, transpiration from the whole plant means the total amount of water that exits the plant collectively through the leaves, and, more preferably, collectively through all the transpiration organs (e.g., leaves, stems, flowers, fruits) of the plant.

As used herein, transpiration rate from the whole plant, the total amount of water per unit time that exits the plant collectively through the leaves, and, more preferably, collectively through all the transpiration organs (e.g., leaves, stems, flowers, fruits) of the plant.

The water fluxes out of the plant and into the plant are utilized according to some embodiments of the present invention to estimate the relative activity of the root system and characterize the plant according to its root functioning under regular and abnormal (e.g., water stress) conditions. The system of the present embodiments optionally and preferably performs automated screening for physiological root performance traits in general and more preferably under drought. In various exemplary embodiments of the invention data collection, analysis and characterization is executed simultaneously for two or more, more preferably many plants. The screening optionally and preferably pinpoint plants showing superior root water uptake under different treatments at different developmental stage and soil types.

The present invention in at least some embodiments provides a system for simultaneously monitoring transpiration rates, and soil water changes in a population of two or more plants and identifying those plants in the population having elevated characteristics relative to other plants as determined from the relationship between their transpiration rates and the water taken up by the plant's roots.

According to some embodiments of the present invention the weight gain of the plant is measured by a weight sensor and used as a proxy to its transpiration rate. Other devices for measuring a parameter indicative of the transpiration rate are also contemplated. For example, an infrared camera can be used to generate a thermal image of the plane and a data processor can analyze the thermal image and estimate the cooling rate of the plant, in which case the cooling rate is used as a proxy to the transpiration rate of the plant.

According to some embodiments of the present invention soil moister or soil water content (SWC) is measured by a soil moisture sensor and used as a proxy to the amount water taken up by the plant. Preferably soil moisture sensor is placed in the vicinity of the plant. Other devices for measuring a parameter indicative of the amount water taken up by the plant are also contemplated. Representative example include, without limitation, an NMR device or an X-ray device for measuring water content in the soil, a tensiometer for measuring soil moisture tension, and the like.

Any of the above devices can be used separately or supplementarily by the system. Preferably, the system includes at least one device or sensor that measures a parameter indicative of the transpiration rate of the plant, and at least one device or sensor that measures a parameter indicative of the amount water taken up by the plant.

The sensors generate time dependent signals which are indicative of the respective parameter sensed by the sensors (weight, water content), and which are optionally and preferably analyzed. In some embodiments the plants are potted plants enclosed in a container containing an amount of water that is in fluid communication with the contents of the pot. In these embodiments, the sensors can be load cells measuring a mass or weight of the container together with the contents of the container, including the water. Transpiration by a plant causes the amount of water in the container to decrease over time which is reflected in a decrease in the mass or weight sensed by the sensor. Thus, by monitoring the mass or weight of the container (e.g., simultaneously for two or more container) over a period of time, a transpiration rate over the time period can be calculated, and by monitoring the SWC over a period of time, the amount and optionally also rate of water usage by the plant are assessed.

In various exemplary embodiments of the invention the signals generated by the sensors over time are processed to determine a transpiration rate and water uptake over two or more time periods. For each time period, the processing may include calculating an average and standard deviation of the transpired water, during this period the ratio between the transpired water and the plant mass gain during this period is extracted. This ratio is referred to as the "water usage efficiency" (WUE) of the plant. Additionally, the water usage is also extracted for each time period by determination of the water absorbed by the plant.

The processing optionally and preferably ranking the plants according to a statistical analysis, for example, ranking the plants according to at least one parameter, such as, but not limited to, the transpiration rate and/or the water uptake rate and/or the difference between the water uptake rate and the transpiration rate and/or the WUE and transpiration in a specific SWC. This allows the identification of plants in the population having preferred characteristics.

The ranking can serve for more than one purpose. In some embodiments of the present invention the ambient condition (temperature, drought level, humidity, light, etc) to which the plant is exposed is controllably varied, and a score is calculated based on at least one of the parameters following the variation. This can be repeated one or more time so that a score describing the characteristics of the plant is associated for each ambient condition. This allows selecting a desired range of ambient conditions that improves the behavior of the plant. For example, when the score is normalized to a number between 0 and 1, any ambient condition for which the score was above a predetermined threshold between 0 and 1 may be defined as ambient condition which is suitable for growing the plant. A representative example of a predetermined threshold is at least one 0.5 or at least 0.6 or at least 0.7 or at least 0.8 or at least 0.9.

In some embodiments of the present invention the plant is a member of a population of plants, and the score is calculated for each plant in the population, for a selected ambient condition. In these embodiments the plants are ranked according to the score wherein the ranking is associated with the selected ambient condition. This allows selecting the best plant or group of plants for the selected ambient condition. The ambient condition can also be varied and the calculation of score and ranking of the plants in the population can be repeated after the variation. This allows selecting the best plant or group of plants also for the varied ambient condition. Ultimately, an output can be generated for providing a list of ambient condition ranges, and a corresponding list of plants or group of plants for which the behavior is expected to improve at the respective ambient condition range.

In one embodiment, the signals are processed over two or more time periods, where each of the two or more time periods is characterized by a set of one or more environmental conditions to which the plant population is exposed. During one time period, the environmental conditions may be control environmental conditions, while during another time period the environmental conditions may be stress conditions. The conditions can be set back to control in order to examine the plants' recovery from the stress. This scenario can be repeated by different combinations of stresses and recoveries. The environmental factors that may be altered between the two time periods include, for example, availability of water, humidity, temperature, irradiation, salinity, soil mineral content) as well as biotic parameters such as bacteria in soil and pathogens. For example, plants having a high rate of transpiration under stressful environmental conditions may be assigned a higher ranking than plants having a lower transpiration under the same conditions. In this embodiment, the processing may further comprise calculating a rate of change of the transpiration rate and water usage upon exposure of the plants to a change in environmental conditions and during the recovery from this stress. The ranking may also involve the rates of change of the transpiration rates and/or water uptake detected when the environmental conditions of the plants are altered. Plants in which the transpiration rate decreases slowly when the environmental conditions become more stressful are optionally and preferably assigned a higher ranking than plants whose transpiration decreased more rapidly. Plants in which the transpiration rate increases rapidly when the environmental conditions become less stressful are optionally and preferably assigned a higher ranking than plants whose transpiration increased more slowly. Plants with higher water uptake during stressful conditions are optionally and preferably assigned higher rank then plant with low water uptake.

In one embodiment, the present invention is used to identify optimal environmental conditions for growing plants. In this embodiment, in each of two or more time periods, the plants are exposed to different environmental conditions.

Ranking of the plants may be done by any one of several methods, enabling different levels of screening. One method involves a comparison of the accumulated weights of target and control plants over a predetermined time period. The weight gain of each individual plant is compared by statistical tools with the average weight gains of the target plant population and the control plants.

In another method for ranking the plants, the cumulative transpiration is used to provide a measure of the amount of water the plant transpires during a given period by summing the daily transpiration and daily water uptake. The cumulative transpiration, and water uptake of each individual plant is optionally and preferably compared to the average cumulative transpirations of the target plant population and control plants, and both are compared to the potential transpiration rate (atmospheric demand).

In another method, the WUE is determined by the cumulative weight gain during a certain period divided by the cumulative transpiration during that period.

The momentary rate of transpiration may be determined from the signal generated by the weight sensor by sampling the signal to obtain a weight time series. The weight time series optionally and preferably smoothed to a certain degree (e.g., subjected to noise reduction) in order to isolate the diurnal transpiration (water loss) trend. The pattern of diurnal transpiration rate is then calculated by a time-derivative (e.g., a first time-derivative) of the variations in smoothed weight. The peak transpiration rate and its timing for each individual plant are optionally and preferably compared with the average peak transpiration rates and timing in the target plant population and control plants, and both are compared to potential transpiration rates.

The momentary rate of water uptake may be determined from the signal generated by the soil moisture sensor by sampling the signal to obtain a moisture time series. The moisture time series is optionally and preferably smoothed to a certain degree (e.g., subjected to noise reduction). The rate of water uptake can then be calculated by a time-derivative (e.g., a first time-derivative) of the variations in moisture time series.

Figure 11:
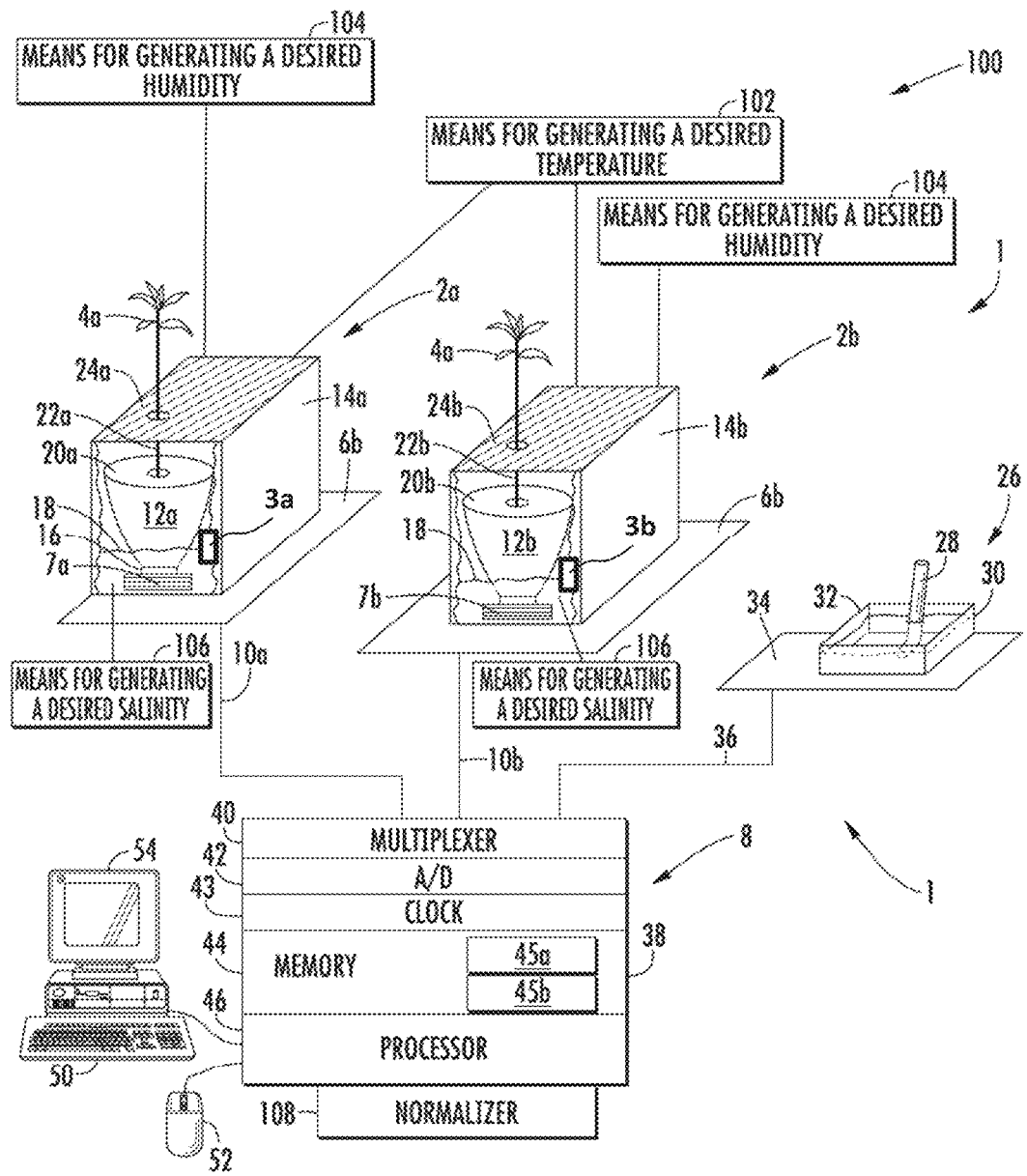
FIG. 11 is a schematic illustration of a system suitable for characterizing one or more plants in accordance with some embodiments of the invention.
Figure 12A:
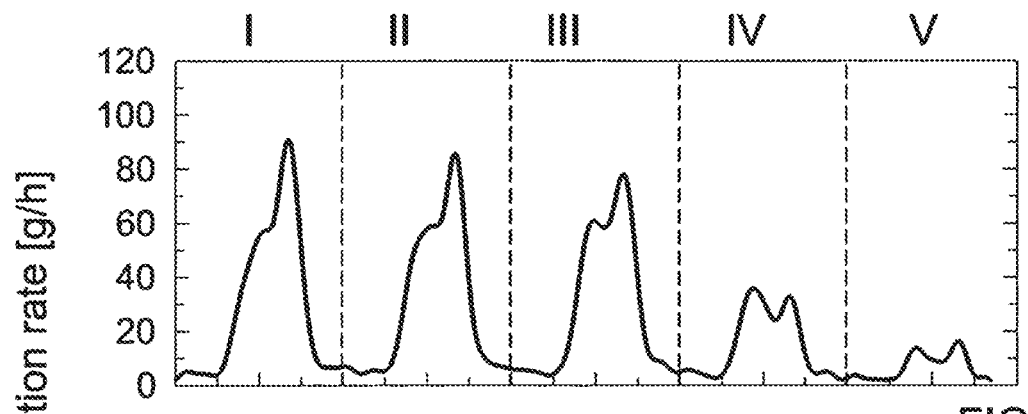
FIGS. 12A-C show transpiration rate of two tomato plants during 5 days of dehydration treatment (FIGS. 12A and 12B), compared to a reference (submerged wick) environmental vapor pressure deficit (VPD), presented in FIG. 12C.
Figure 12B:
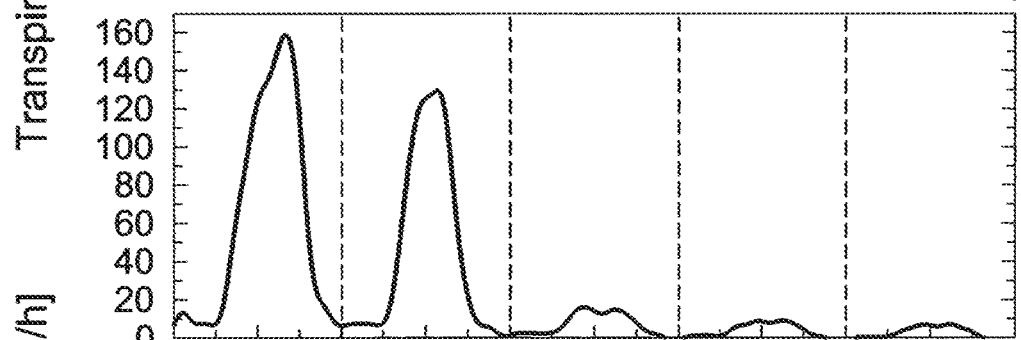
Figure 12C:
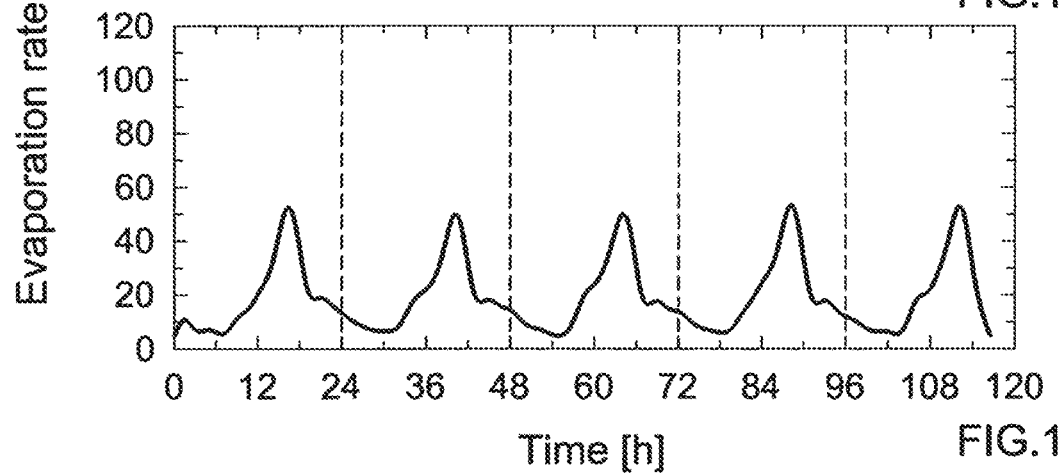

Referring now to the drawings, FIG. 11 is a schematic illustration of a system 1 for simultaneously monitoring transpiration rates in a plant or a population of two or more plants, in accordance with at least some embodiments of the present invention. System 1 optionally and preferably also identifies those plants in the population having elevated characteristics relative to other plants.

The system 1 comprises one or more monitoring units 2, where each monitoring unit 2 serves to monitor the transpiration rate and water uptake in a respective plant 4. For simplicity, and by way of example only, two monitoring units, 2a and 2b are shown in FIG. 11. Typically, the system 1 will be configured to include a number of monitoring units 2 equal to the number of plants in the population to be monitored.

Each monitoring unit 2 optionally and preferably includes two or more sensors 3, 6 sensing one or more parameters related to the plant. In FIG. 11, which is not to be considered as limiting, unit 2a includes a sensor 3a and a sensor 6a, and unit 2b includes a sensor 3b and a sensor 6b. Each sensor 3, 6 generates a time dependent signal indicative of the respective measured parameter sensed by the sensor, which is transmitted to a processing station 8 for further processing as, explained below. Communication between a sensor 6 and the processing station 8 may be via a wired communication channel, as shown in FIG. 11, where each of the sensors 6 is connected to the processing station 8 by a communication line 10, which may optionally be wired. Alternatively, the sensors may communicate with the processing station 8 over a wireless communication channel. In a preferred embodiment shown in FIG. 11, the plants 4 are potted plants, held within a pot 12, and each pot 12 is enclosed in a container 14. The containers 14 are shown in FIG. 11 in a cut-away view in order to reveal the pot 12 and the portion of the plant 4 contained in the container 14. Each pot 12 contains a growth medium that may be solid, such as soil or an artificial growth medium, or may be a liquid as in the case of hydroponic plant growth.

Sensors 3 can be moisture sensors placed in the soil, optionally and preferably in the vicinity of the plant's root. Each container 14 contains an amount of water 18 that is in fluid communication with the contents of the pot 12 via holes 16 in the pot 12. In this preferred embodiment, the sensors 6 are load cells measuring a mass of the container 14 together with the contents of the container, including the water 18, and sensors 3 are placed in the soil that is inside the pot. Transpiration by a plant 4 causes the amount of water 18 in the container 14 to decrease over time which is reflected in a decrease in the mass sensed by the sensor 6.

The load cell can be calibrated to indicate an absolute weight of the cell or a weight relative to a baseline or a change of weight relative to a baseline or relative to a previous weight measurement. The load cell is preferably sufficiently sensitive enough to detect very fast (e.g., within 10 minutes or less, or within 1 minute or less, or within 10 seconds or less, or within 5 seconds or less or within 1 second or less) changes in the weight, and very small changes in the weight (e.g., changes of less than 1 gr, or less than 0.1 gr or less than 0.01 gr).

In a test situation, preferably a plurality of containers 14 and plants 4 are provided. Once a day (usually at night when the transpiration rate is very low) the containers 14 are filled with water to a predefined level (depending on the applied stress), one or more containers 14 are not filled along a drought stress period, or may be filled with salty water during a salinity stress period, and so on. The pots 12 are optionally and preferably covered with a cover 20 through which the stem 22 of the plant passes in order to reduce or prevent evaporation of water from the contents of the pot. Similarly, each container 14 is optionally and preferably covered with a cover 24 through which the stem 22 passes in order to prevent evaporation of water from the container 14.

Thus by monitoring the mass of the container 14 over a period of time, a transpiration rate over the time period can be calculated at the processing unit 8, and by monitoring the SWC the water uptake rate can be calculated as explained below.

Sensors 6, when implemented as load cells, may also be used to monitor a mass of the pot 12 together with its contents including the plant 4. As the plant 4 grows, the mass of the plant 4 increases, and by monitoring the mass of the pot 12, so that monitoring the mass of the pot 12 over a time period allows a growth rate, and hence yield, of the plant to be calculated over the time period at the processing station 8, as explained below.

The system 1 optionally and preferably further comprises a device 26 to determine atmospheric demand for water. The device 26 comprises a wick 28 preferably made from a woven fabric. A portion of the wick 28 is submerged in water 30 in a container 32, corresponding to the below described "wet wick". Most of the wick 28 is optionally and preferably exposed to ambient air so that water absorbed into the wick 28 from the container 32 can evaporate off of the wick. The device 26 further comprises a sensor 34 which is a load cell, for monitoring a mass of the container 32 and it contents. The load cell 34 generates a time dependent signal indicative of the mass of the container 32 and its contents that is communicated to the processing station 8 over a communication channel 36 that may be a wired channel or a wireless channel. The container 32 is optionally filled daily by water to a predefined level.

The system 1 may optionally include additional sensors (not shown) such as sensors to monitor canopy temperature over time, the water content or the water potential in the pots 12. Also contemplated are other external sensors (not shown) for measuring at least one of ambient light, ambient temperature and ambient relative humidity.

One or more of the sensors (e.g., sensors 3, 6 and 34) generates a time dependent signal that is communicated to the processing station 8. The processing station 8 includes a CPU 38 including a multiplexer 40 that sequentially sends each of the input signals to an analog to digital converter 42 that samples the input signals at predetermined times and at predetermined frequencies. The sampling frequency may be for example, every 12 hours, more preferably, more preferably, more preferably, even more preferably, still more preferably, every two hours, every hour, every 10 minutes, 5 minutes or every minute, every 30 seconds or every 10 seconds. A higher sampling frequency allows a shorter sampling time that tends to reveal the momentary transpiration rate that includes oscillations in the transpiration rate that might otherwise be overlooked with lower sampling frequencies. The samples of the digitized signals are time stamped by means of a clock 43, and the time stamped samples are stored in a memory 44 of the CPU. Each signal is stored in a file 45 in the memory 44 that is addressable by an identifier of the monitoring unit at which the signal was generated. The CPU contains a processor 46 configured to process the signals stored in the memory 44. The processing preferably includes filtering device-related noise from the signals.

For the signals generated by the load cells 6, the processing optionally and preferably includes calculating a transpiration rate by the plant 4 of the monitoring unit, for example, by calculating a time derivative of the filtered signal. For the signals generated by the moisture sensors 3, the processing optionally and preferably includes calculating a water uptake rate by the plant 4, for example, by calculating a time derivative of the filtered signal.

The processing may also include calculating a growth rate of the plant 4 at the monitoring unit, for example, by calculating a time derivative of the signal. The processing may also include comparison of a calculated transpiration rate with an evaporation rate from the wick 28. The processing may also include calculating a ratio between each plant's transpiration rate with its growth rate. The processing may also include calculating the root water uptake of plant 4 as the time derivative of the SWC.

In some embodiments of the present invention the processing includes calculating variability in leaf Relative Water Content (RWC), and classifying the plant into a classification group which is one of: (i) a classification group of plants exhibiting isohydric behavior, and (ii) a classification group of plants exhibiting anisohydric behavior. For example, when the variability in leaf RWC for a particular plant is higher than a predetermined RWC variability threshold, the processor can classify the plant as anisohydric and when the variability in leaf RWC for a particular plant is lower than a predetermined RWC variability threshold, the processor can classify the plant as isohydric. The RWC variability threshold can be expressed in percentage. Representative RWC variability thresholds suitable for the present embodiments including, without limitation, about 5% or about 10% or about 15% or about 20%.

The determination of the RWC variability is preferably over a predetermined time period, which can be, without limitation, from about one hour to about a day. Thus, for example, when the leaf RWC changes by more than P % relative to a baseline RWC over the predetermined period, the processor the processor can classify the plant as anisohydric, and when the leaf RWC changes by less than P % relative to the baseline RWC over the predetermined period, the processor the processor can classify the plant as isohydric, where P is from about 5 to about 20. The baseline RWC can conveniently be set to 100%, but any other baseline level can be selected.

The variability in RWC can be calculated based on the root uptake rate and the transpiration rate. In some embodiments of the present invention the difference between the root uptake rate and the transpiration rate are integrated over time and the result of the integration is divided by weight of the plant to determine the variability in RWC. The integration is preferably but not necessarily a discrete integration. A representative example of such calculation is provided in the Examples section that follows.

The processing station 8 also optionally and preferably includes user input device 48 that may be keyboard 50 or a computer mouse 52 that allows the user it input into the memory 44 any relevant information, such as an identifier of the plants 4 at each of the monitoring units, the environmental conditions under which the signals were obtained. A display device 54, serves to display any of the input signals or the results of any of the processing.

In accordance with at least some embodiments of the present invention, the processing of the signals is performed over each of two or more time periods. Typically, each of the two or more time periods is characterized by a set of one or more environmental conditions to which the plant population is exposed. During one time period, the environmental conditions may be control environmental conditions, while during another time period the environmental conditions may be stress conditions. The system 1 may thus further comprise means (not shown in FIG. 11) for generating desired conditions in the environment of the plants 4. Such means may include means for generating a desired temperature, humidity, water salinity, and so on.

The processor 46 may be configured to normalize the transpiration rates to the surface area of the leaves of each plant, or to the density of stomata in the leaves. The surface area of a leaf may be determined using a scanner as is known in e art.

For each time period, the processing may optionally and preferably include calculating an average and standard deviation of the transpiration rates, or the ratio between the transpiration rate and the growth rate, observed in the population over the time period. The processing may optionally and preferably also include smoothing any fluctuations or other noise in the signals according to any art known method, as described in greater detail below. However, it should be noted that the signals may still oscillate, representing oscillations in the plants' transpiration rates, rather than noise.

The processing may optionally and preferably further include ranking each of the plants in the population according to the statistical analysis, for example, ranking the plants according to their transpiration rate or according to their ratio of their rates of transpiration and growth root uptake and stress tolerance. Optionally, differences between smoothed transpiration rate patterns and, addition or alternatively, oscillatory transpiration rate patterns are compared between a plurality of populations of plants, which may for example optionally differ according to species, strains within species or genetically modified versions of such strains; for the last option, optionally one or more genetically modified versions of a particular strain are compared to the non-modified strain or to other version(s) of the modified strain.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

An experimental study was conducted using the system of the invention in greenhouses at the Faculty of Agricultural, Food and Environmental Quality Sciences, Rehovot, Israel. The system included 3.9 liter growing pots that were placed on temperature-compensated load cells (Tadea-Huntleigh, Israel) that were connected to a CR10 data logger (Campbell, scientific inc. USA). The pots were filled with a commercial growing media (a mixture of peat and tuff scoria) and a single plant was grown in each pot. Each pot was immersed in a plastic container (13×21.5×31.5 cm H W L) through a hole in a top cover of the container. The tops of the pots and the containers were sealed by aluminum foil to prevent evaporation. Under conditions of high irrigation, the container was filled daily to a height of 2 cm above the pot base Irrigation with excess water tended to leach salts accumulated in the growing media during each day. A commercial fertilizer solution 0.2% (Super Grow, Hortical Israel) was added to the irrigation water, a process referred to herein as "fertigation". Fertigation ensures that a) the plants are not subjected to water stress, and b) the container-weight during day decreases monotonically only by plant transpiration.

Pot weight readings, taken every 10 s, were averaged over 3-min periods. This averaging period is lower than the oscillation frequency (20 to 40 min) and is higher than the Nyquist frequency (the highest frequency about which meaningful information can be obtained from a set of data), and was found to have a minor effect on the oscillations. The load-cell readings stabilized after 2 s, following excitation by dropping a 70 gr steel ball from a height of 700 mm (manufacturer's data). Thus, a 10 sec weight-sampling interval ensured that the maximum rate of weight decrease of 0.5 g per 10 sec was appropriately followed.

In order to identify and isolate any noise introduced by the measuring and data acquisition systems from short-term fluctuations in plant transpiration rates, a constant weight of about six kg (about equal to the mass of the container+pot+ plant) was placed on load-cells in the greenhouse for two days.

Plants

Tomato plants (*Solanum lycopersicom* previously known as *Lycopersicon esculentum* L.) were grown in both controlled-environment and commercial greenhouses in a light cycle consisting of 14 h light and 10 hours dark. The temperature in the controlled environment greenhouse was 18° C. during the night hours and 35° C. during the midday hours, gradually varying between these two extreme temperatures. The ambient conditions in the commercial greenhouse were controlled by a fan with a wet-mattress. Abscisic acid (ABA) deficient lines sitiens cultivar (Ailsa Craig the background as near-isogenic lines, the kind gift of Dr. Andrew J. Thompson) and the poplar plants (*Populus alba*) were grown in the commercial greenhouse. Four month old shoots re-grown from one year old poplar plant cuttings (about ten centimeters above the growing media surface) were used in these experiments.

Cut tomato shoot experiments were performed by excising the root of two wild type tomato plants out of five plants that had been placed on the load cells. The root removal was done while submerging the plant in tap water in the evening in order to prevent penetration of air bubbles into the xylem. The tomato shoot was then immersed in a container containing 2 liters of tap water that was placed on the load cell. The dehydration conditions were created by stopping the irrigation for six days.

Leaf area measurements; tomato leaves were cut immediately after the experiment ended and scanned using an automatic scanner (Li cor, model Li 3100 area meter). The poplar leaf area was measured without excising the leaves using a portable leaf area scanner (Li cor, model Li-3000A).

Weight loss from a vertically hanging woven rag (0.14 m$^2$) whose lower end was dipped in water (referred to herein as the "wet wick") was measured. The rate of weight loss from the wet wick provided an assessment for the momentary atmospheric demand. The noise associated with the weight decrease of the wet wick was also used to indicate noise levels associated with the load-cell response to dynamic monotonic weight variation. The data from the load cells with plants, wet wick and constant weight data were analyzed by a time series analysis explained below.

Data Analysis

The rate of water loss from the container, being the negative value of the whole-plant transpiration (WPT) rate, is calculated by the first derivative of the measured-weight time series $$WPT \equiv -\frac{dW}{dt} \approx -\frac{W_{k+1} - W_k}{t_{k+1} - t_k} \quad (1.1)$$

where $W_k$ and $W_{k+1}$ is the measured weight of the container at time $t_k$ and the subsequent time step $t_{k+1}$. In general, differentiation acts as a high-pass filter, and thus significantly amplifies the high frequency noise. Noise can be reduced or eliminated by smoothing (detrending) the measured data (time series) so that it becomes stationary prior to spectral analysis. The differentiation of a leading variation pattern provides a smoothed pattern WPT rate. Any method can be used for smoothing the data including non-parametric smoothing (e.g. moving average, Savitzky-Golay, and FFT filtering) and non-parametric regression (fitting polynomials of various orders, exponential functions, symmetrical and asymmetrical transition functions, etc. to the measured data).

It is assumed herein that the container-weight time series follows an additive model $$W_k = W(t_k) + \varepsilon_k, \ 1 \le k \le n \ t_1 < t_2 < \ldots t_k \ldots < t_n \quad (1.2)$$

where W is the weight at time $t_k$ would have if it varied smoothly with time, and $\{\varepsilon_k\}$ is the deviation from that value. The system weight oscillations superimposed on the smoothed time series are also a time series, and are designated as the 'residual time series' (residuals are the differences between the measured data and the fitted curve). When the mean of the residuals time series is zero, the trend of the measured time-series was properly removed. We presume that the residual time series $\varepsilon_k$ (Eq. 2) is a superposition of two time series; one is made of residuals that originate from the data acquisition and other system-related noises, $\varepsilon_{k_1}$, and the other from residuals originated from the intrinsic oscillations in WPT, $\varepsilon_{k_2}$. The independently measured time series for the constant weight, wet wick and plant runs were used to study the properties of $\varepsilon_{k_1}$ and $\varepsilon_{k_2}$ and examine their randomness (white noise) by the autocorrelation function.

The spectrum analysis of $\varepsilon_k$ was used to explore the existent of cyclical patterns. The spectral analysis decomposes a complex time series with cyclical components into a few underlying sinusoidal (sine and cosine) functions of particular wavelengths. By identifying the important underlying cyclical components, the characteristics of the phenomenon of interest could be realized, namely, identify the wave lengths and importance of underlying cyclical component in the WPT rate. This spectrum analysis reveals cycles of different lengths in the time series.

The spectrum (amplitudes vs. frequencies) of the residual time series was calculated by the Fast Fourier Transform (FFT), which decomposes a time-domain signal or time series into complex exponentials (sines and cosines). The spectrum of the constant-weight residual time series, $\varepsilon_{k_2}$, will be used to determine the frequency threshold that will be used to filter out the high frequency noises (low-pass filter) from the plant-weight residual time series, $\varepsilon_{k_1}$. Subsequently, the filtered spectrum is reconstructed back to a time series (in the time domain) by the inverse FFT. The time derivative of the reconstructed low-pass-filtered time series d ($\varepsilon_k'$)/dt ($\varepsilon_k'$ low-pass filter of $\varepsilon_k$) provides the oscillatory transpiration rate that superimposes the smoothed WPT rate.

Experiment 1

Oscillations in Whole-Plant Transpiration (WPT) Rate

Figure 1B:
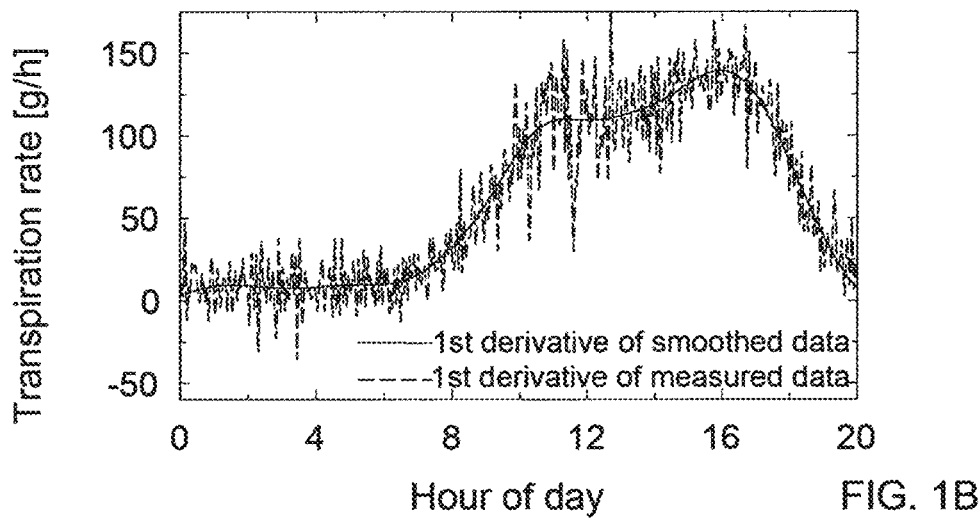
FIG. 1B shows the calculated whole-plant transpiration (WPT) of the plant of FIG. 1A.

A typical measured weight variation by transpiration during the night and subsequent day hours is shown in FIG. 1A for a control tomato plant that was grown in the temperature-controlled greenhouse. The WPT rate was calculated by the time-derivative of the measured weight time series (Eq. 1) as shown in FIG. 1B. This time derivative is noisy despite the apparent relative smooth weight-decrease pattern (FIG. 1A). The noise amplitude was lower during the night and early morning hours, increased afterwards, reached a maximum during the late morning and early afternoon hours, and decreased again during the evening hours. Weight fluctuations around the smoothed pattern has usually been considered as a random signal (white noise) that does not contain useful information regarding the pattern of transpiration rate and its dependent on ambient conditions, and were therefore ignored during the data-smoothing process.

Alternatively, the WPT rate was calculated by first smoothing the weight time series and then calculating the time derivative (FIG. 1B). The measure-weight time series was smoothed by the Savitzky-Golay (S-G) method using a 30 data point window breadth. This smoothing method is based on a least-square quadratic polynomial (although higher orders can be also used) fitting across a moving window within the data. The S-G method can be applied for various breadths of filtering windows, and it is considered a very good way to produce accurate smooth derivatives, an advantage for the current study where the transpiration/evaporation rate were determined by a derivative of the weight decrease. Very high $R^2$ values were obtained with the S-G method for wide range of filtering window breadths, and the fit improves as the filtering window breadth is decreases. Nevertheless, as the filtering window breadth decreases, the predicted water uptake patterns include fluctuations of lower frequencies and higher amplitudes, and for very narrow windows $R^2 \to 1$, which means that the smoothed curve passes through all data points, and the pattern of the derivative is identical to that obtained by numerical differentiation of the measured data (FIG. 1B). The time-derivative of the data time series that was previously smoothed by S-G method with for a whole plant is shown in FIG. 1B.

Figure 2A:
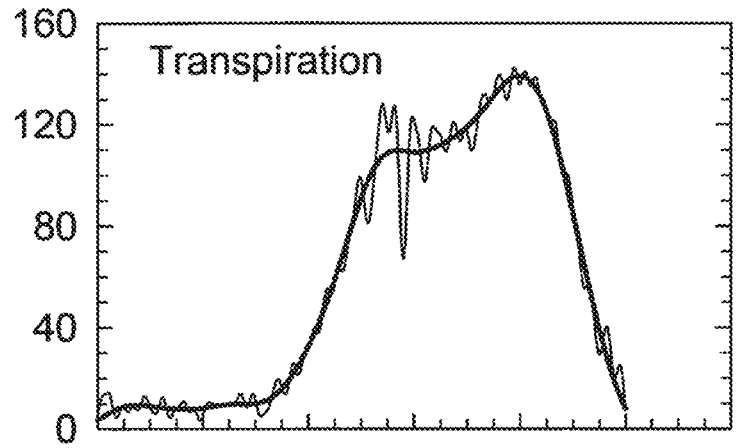
FIGS. 2A-C show the average and the superimposed oscillations in the rate of weight variation for a plant, wet wick, and constant weight, respectively.
Figure 2B:
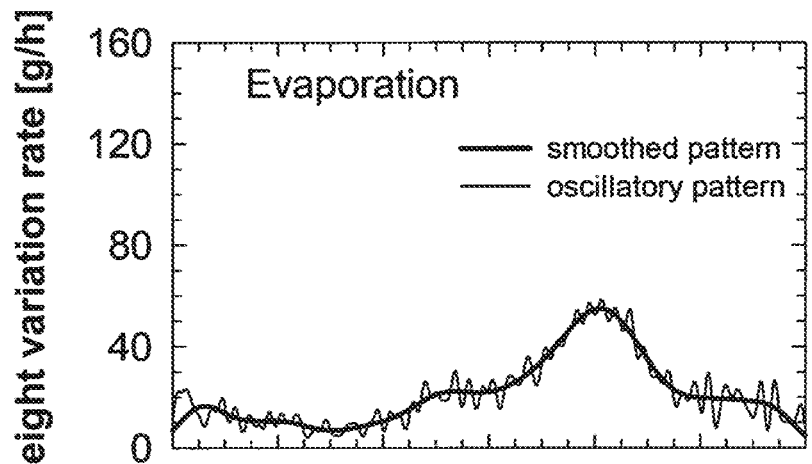
Figure 2C:
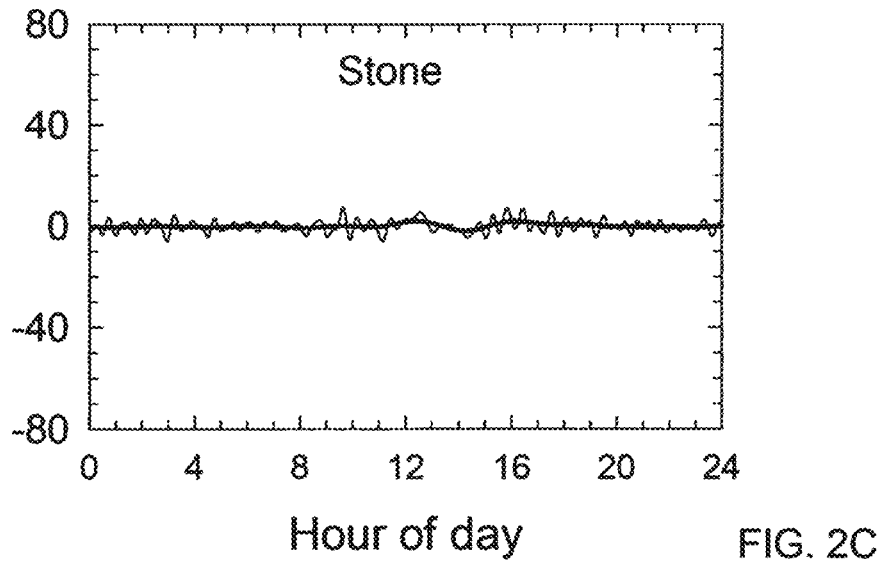

The average and the superimposed oscillations in the rate of weight variation for the whole plant, wet wick, and constant weight are shown in FIG. 2A, B, C, respectively. The method to calculate the oscillatory transpiration rate is demonstrated in the sequel. The different oscillatory pattern for the whole plant, wet wick, and constant weight indicate that oscillations in WPT rate are indeed a physiological phenomenon, independent of noises in the load cell and data acquisition system or direct fluctuations in the ambient conditions.

To exclude the possibility that the oscillations in WPT rate are system and environmental noises, the residual (difference between the measured data and the data smoothed by the S-G method time series) for the whole plant, wet wick, and constant weight were examined for randomness (white noise) by calculating the autocorrelation of the signals. The autocorrelation functions for the three cases are shown in FIGS. 3A,C,E, respectively. The autocorrelation function of the controlled-weight residual time series, $\varepsilon_{k_1}$, (FIG. 3E) has a strong peak at lag=0 and is close to zero for all other lags. This shape indicates that $\varepsilon_{k_1}$ can be considered as white noise. On the contrary, the autocorrelation function of the whole-plant residual time series, $\varepsilon_{k_2}$, (FIG. 3A) is periodic for the first 200 lags, with an average of 40 lags difference from peak to peak. This indicates that the whole-plant residual time series is distinguishable from white noise. The autocorrelation function of the wet wick (FIG. 3C) indicates that residual time series for this data is not random as well. The deviation from randomness in this case can be related to changes in the ambient conditions in the greenhouse. The notable differences between the autocorrelation functions for the whole plant and the wet wick (FIGS. 3A and C, respectively) and between both and that of the constant weight (FIG. 3E) indicate that the residual time series of the whole plant contains a non-random noise associated with oscillatory plant transpiration pattern that superimpose the smoothed weight decrease pattern, beyond the superimposed fluctuations in wet-wick evaporation.

An additional test for randomness is the spectral analysis that was also used to filter the white (random) noises from the "colored" noises. The spectra for the whole-plant, submerge-wick, and constant-weight residual time series are shown in FIGS. 3B, D, and F, respectively. The overall flat spectrum of the constant-weight (FIG. 3F), indicates that its residual time series is practically a random signal (white noise). The spectrum for the whole plant (FIG. 3B) has high amplitudes at frequencies below 2.5 $h^{-1}$ and lower amplitudes at higher frequencies. The wet-wick spectrum has high amplitudes (still lower than the whole plant) at frequencies below 2 $h^{-1}$ and lower amplitudes at higher frequencies. In order to filter the white noise, both spectra were low-pass filtered using a cut of filter passing frequencies below 2 $h^{-1}$ prior to further analysis. The time derivative of the reconstructed low-pass filtered residual time series revealed oscillations in WPT rate for the plants and in the evaporation rate of the wet wick that superimpose the average transpiration/evaporation rates, respectively (FIG. 2A,B). Similar results as in FIGS. 2A-C and 3A-F were obtained for different days and plants for different ambient conditions.

The Effect of Drought on Oscillations in WPT Rate Pattern

Figure 4A:
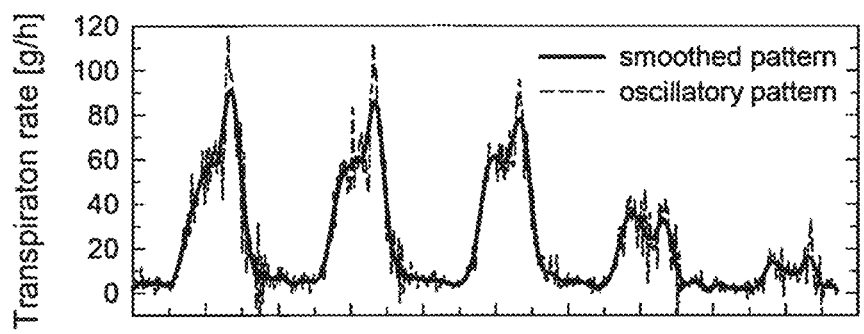
FIG. 4A shows the effect of five days of dehydration on the momentary WPT rate (smoothed oscillatory)
Figure 4B:
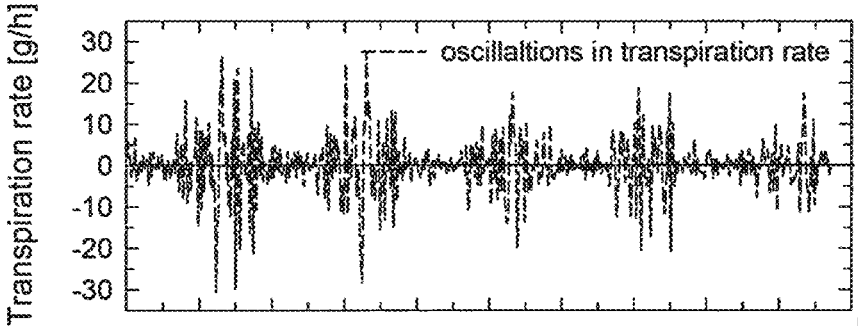
FIG. 4B shows the oscillation patterns observed in the WPT rate superimposed on the smoothed pattern of FIG. 4A.
Figure 4C:
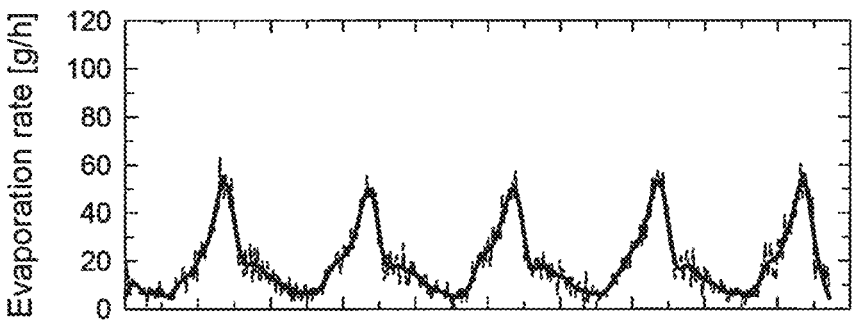
FIG. 4C shows the smoothed and oscillatory evaporation rate from the wet wick.
Figure 4D:
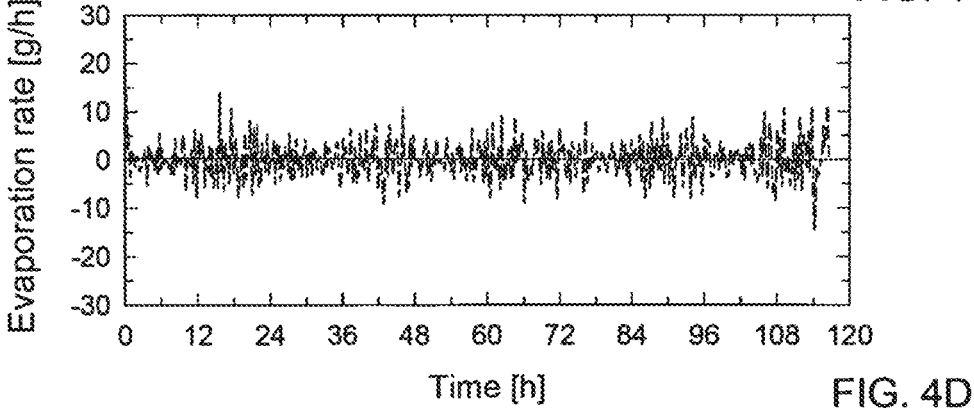
FIG. 4D shows the oscillation pattern in evaporation superimposed on the smoothed pattern of FIG. 4C.

The effect of five days of dehydration, obtained by a gradual depletion of the water in the growing medium, on the momentary WPT rate (smoothed oscillatory) is shown in FIG. 4A. The oscillation patterns observed in the WPT rate that was superimposed on the smoothed pattern in FIG. 4A are individually shown in FIG. 4B. The last irrigation was provided on the evening proceeding the first day in FIGS. 4A-D. For comparison, the smoothed and oscillatory evaporation rate from the wet wick are shown in FIG. 4C and the oscillation pattern in evaporation that was superimposed on the smoothed pattern in FIG. 4C are individually shown in FIG. 4D. FIGS. 4A-D show that: 1) Water was available to the plant during the first two days to meet the atmospheric demand and the characteristic patterns of the smoothed and oscillatory WPT rate are similar to those shown in FIG. 2A. The smoothed transpiration rate pattern has two peaks during each day (FIG. 4A); a lower peak in the morning and a higher peak in the afternoon. 2) The transpiration rate substantially decreases during the last two days, due to water depletion in the growing medium. The two peaks on each of these days had similar heights with a noticeable dip between them. As opposed to the daily two-peak pattern in the whole plant, there was one peak of a constant value in the smoothed wet-wick evaporation rate (FIG. 4C). The timing of the single daily peaks coincided with the second peak in the smoothed WPT rate. 3) The oscillation pattern in WPT rate is substantially different than that of the wet-wick evaporation rate which had uniform amplitude values during the day hours that were slightly different than those of the night hours (FIGS. 4C, 4D). In contrast, the daily oscillation pattern for the WPT rate varied significantly with time. It was low during the nigh hours, started to increase at about 9:00 AM, intensified toward midday and early afternoon at which time the VPD and transpiration rate were high, and gradually decreased during the later afternoon hours (FIGS. 4A, 4B). The substantial difference in the oscillation amplitudes between WPT and evaporative rates among the day and night hours (FIGS. 4B and 4D, respectively) indicates that the oscillation in WPT rate is an intrinsic physiological process associated with varying ambient environmental conditions. 4) The amplitude of the oscillations in WPT rate depended on water availability, as can be seen in the last two days in FIGS. 4A, 4B. Their value relative to the smoothed transpiration rate during the midday hours were much higher than during the first three days. 5) Unexpectedly, oscillatory night transpiration rate patterns were observed (FIGS. 4A, 4B); it was higher during the first three nights and approached zero during the subsequent two nights.

Whole Plant vs. Excised Shoot

The smoothed WPT rate and the superimposed oscillations for a typical tomato whole plant, excised shoot, and evaporation rate and the superimposed oscillations for the wet wick are shown in FIGS. 5A-F. FIG. 5D show results for the shoot of the "mother" plant whose results are shown in FIG. 5C. As opposed to the two-peaks daily pattern of the smoothed WPT rate (FIGS. 2A-C, 4A-D, and 5A-C), the smoothed transpiration rate pattern for excised shoot (FIG. 5D) had a single peak in the morning that followed by a monotonic decrease in transpiration rate. As seen before (FIGS. 2A-C and 4A), the daily second peak in WPT rate coincided with the single peak of the wet wick (FIGS. 5E, 5F). Note that the single peak in FIG. 5D is higher than the momentary transpiration rate of the whole plant at that time (FIG. 5B), and at the same time on day before (FIG. 5A, 5C), probably due to the root resistance to flow in the whole plant. The oscillations pattern and amplitudes in shoot transpiration rate (FIG. 5D) were in general similar to those obtained for the evaporation rate from the wet wick (FIG. 5E, 5F) and both are lower than those of the WPT rate (FIGS. 5A-C).

ABA Deficient Mutants

Representative results of oscillatory and smoothed WPT rate for an ABA-deficient sitiens plant and a control plant and evaporation rate and the superimposed oscillations for the wet wick are shown in FIGS. 6A-C. Since two different plants are compared, the transpiration rate was normalized to the leaf area of the individual plant and the wet wick to its own surface area. The sitiens mutants, shows significantly higher daily transpiration rate when compare to control (FIG. 6A). These plants show unique and much higher amplitudes and frequency oscillations pattern compared to the control plants. These oscillations started at dawn and persisted throughout the day (FIGS. 6B and 6C). Although the sitiens plants lose turgor around nine AM in the morning it continued to transpire through the day, and retain turgidity during the night.

Comparison with Poplar as a Higher Xylem-Vulnerable Plant

Representative results of oscillatory and smoothed WPT rate for two poplar (*Populus alba*) plants and the evaporation rate and superimposed oscillations for the wet wick are shown in FIGS. 7A-D. The transpiration rate was normalized to the leaf area of the individual plants. The relative low transpiration rate of poplar was (approximately the same as wick) due to their small size (FIGS. 7A-D). The oscillation patterns of poplar plants differed substantially from those of control tomato plants (FIGS. 2A-C, and 4A-6C) but was similar to those of sitiens plant (FIGS. 6A-C). As could be detected from the post-dawn oscillations in WPT (FIGS. 7A-D), the oscillations had intensified and kept the same pattern throughout the day hours. This transpiration rate pattern (including oscillations) could be related to the differences in the cavitation vulnerability stress between tomato and poplar.

Experiment 2

Testing Isogenic Tomato Mutations for Transpiration Patterns

The method of the invention was used on an isogenic tomato 'Mutation Library' in the genetic background of the inbred variety M82. Field prescreening of this library yielded 29 mutants lines that showed a wilting response even under well watered nutrient-supply conditions. The amount of members in each line varied from 1 to 11, all together 350 individuals.

The screening method included six highly sensitive, temperature-compensated load cells (weighing lysimeters) that were connected to a data-logger and sampled every 3 minutes. Single potted plants were located on the load cells for 1-2 days. The time was decided upon the ability to identify the transpiration pattern of the tested mutants compared to control plants and submerged wick (proving information on the atmospheric demand). Evaporation from the pot surface was prevented by covering the growing-medium surface with an aluminum foil. The plants were fertigated every evening. The pots were submerged in container in order to keep constant water availability to the roots. From 350 plants, two individual plants representing two mutant lines were identified.

The two plants (chosen from the 42 plants on the array which are simultaneously monitored in the greenhouse) present two different patterns of transpiration rate (strategies) during the drought treatment. This figure presents one of the five criteria used by PLANTarray during the high-throughput selection process (see Materials and Methods).

Figure 8A:
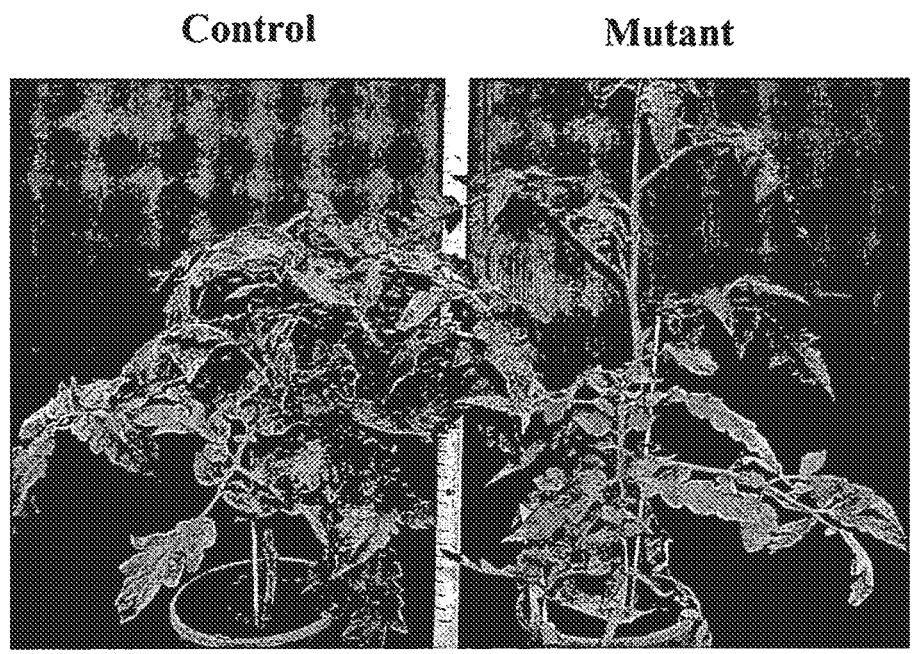
FIGS. 8A-B show a control plant and a mutant plant.
Figure 8B:
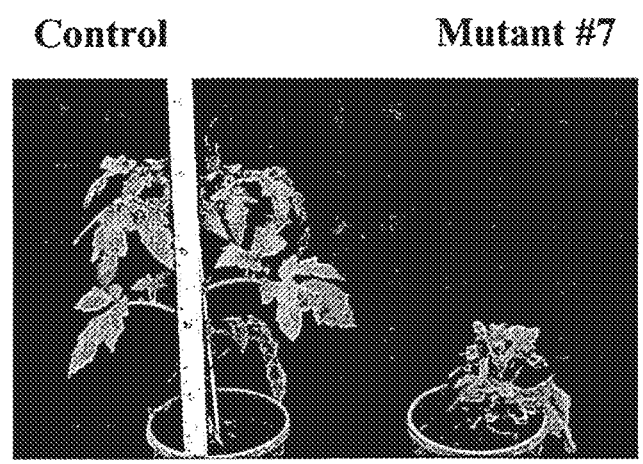
Figure 9A:
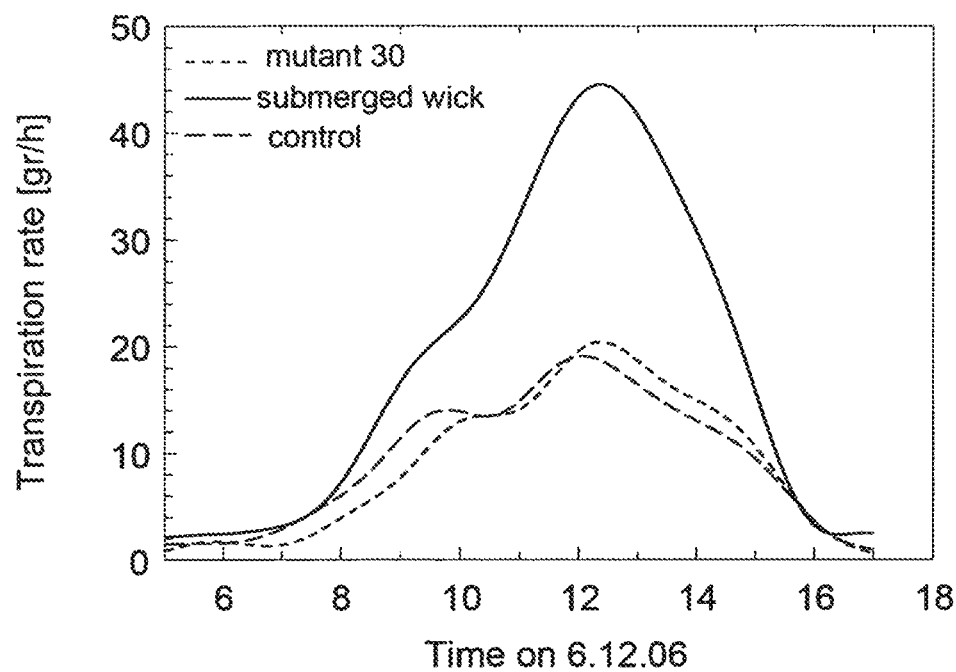
FIGS. 9A and 9B show transpiration from the control plant and the mutant plant of FIGS. 8A and 8B, respectively.
Figure 9B:
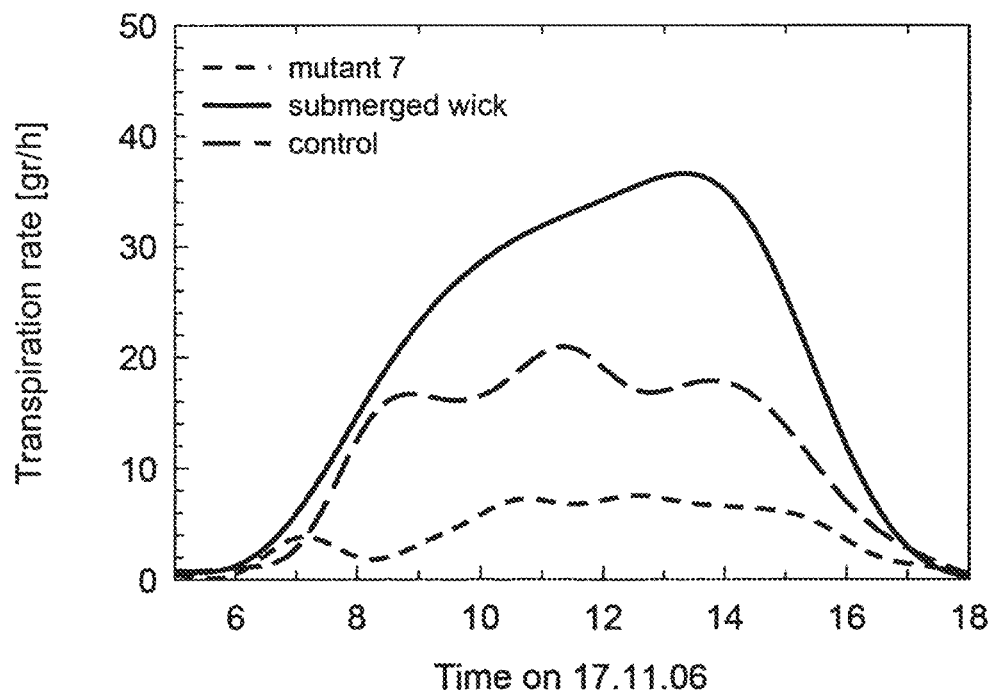

Mutant #30, with a leaf area 40% lower than the control plant (FIGS. 8A-B) transpired similar water amounts (FIG. 9a), namely higher transpiration rate per leaf-area unit. Mutant #7, with a much smaller leaf area than the control plant (FIGS. 8A-B) transpired much less than the control (FIG. 9b). Looking for the causes of the transpiration differences among the mutants, we found significant changes in stomata pore size (FIG. 10) and density. The mean number of stomata of mutant #7 were significantly lower ($11\pm0.16$; Mean$\pm$SE, N=29) per 0.1 (mm)2 leaf size in compare to control ($17\pm0.14$; Mean$\pm$SE, N=29) while the other mutant (#30) had significantly higher number of stomata ($23\pm0.16$; Mean$\pm$SE, N=29) per 0.1 (mm)2 leaf. The mean stomata pore size of mutant #30 were significantly smaller ($11.86\pm6.3$; Mean$\pm$SE, N=29) in compare to control ($26.94\pm12.4$; Mean$\pm$SE, N=29) where the mutant #7 mean stomata pore size were significantly higher ($66\pm12.4$: Mean$\pm$SE, N=29; P value=0.001).

These results allowed the identification of stomata-defective mutants in a population of 350 plants after about 8 weeks of monitoring which is significantly shorter than conventional field screening methods.

Example 2

The regulation of different strategies used by vascular plants for managing their water budgets in the face of fluctuations in soil water availability and atmospheric demand for water is not well understood.

This Example relates to a study performed on the kinetics and dynamics of water homeostasis regulation in isohydric and anisohydric tomato (*Solanum lycopersicum*) lines, in response to imbalances between soil water availability and atmospheric demand. The plants' behavior was characterized under particular environmental conditions using a novel system for the continuous monitoring of the whole-plant transpiration rate, root-to-shoot water flux ratios by the difference between transpiration rate and root water uptake derived from weighting unit and SWC, in addition to ambient radiance and the vapor pressure deficit. These measurement data were collected from tens of plants simultaneously, supporting the calculation of the whole-plant stomatal conductance, water-use efficiency, relative water content variation and hydraulic conductance of all of the plants (relative water content variation is calculated taking into consideration also root water uptake). Expression profiles of several aquaporins (AQPs) from both cultivars across a range of SWC levels revealed differences in the expression of two tonoplast AQPs (TIN) and one plasma membrane AQP (PIP).

This Example shows that the dominant feature distinguishing isohydric from anisohydric behavior is the variability in leaf relative water content (RWC). In both lines, leaf water potential decreased as drought developed. However, in the isohydric line, the RWC fluctuated within a narrower range than in the anisohydric line. The dynamic buffering role of the vacuole, particularly its TIPs, on the regulation of leaf water status and the uninterrupted supply of water for transpiration is also described below.

Materials and Methods

Experimental Setup

This study was conducted in greenhouses located at the Faculty of Agriculture, Food and Environment in Rehovot, Israel during December 2011 and June 2012 (referred to as winter and summer experiments, respectively). In the greenhouses, plants were kept under natural light conditions and vents and/or cooled moist air were used to ensure that the maximum temperature in the greenhouse did not exceed 35° C. The temperature and relative humidity were in the range of 25-35° C. and 40-60% during the summer experiment and 18-35° C. and 20-35% during the winter experiment. The experimental setup included 42 3.9-L pots placed on temperature-compensated load cells (1042 C4; Vishay Intertechnology, USA). The pots were filled with a commercial growing medium (Matza Gan; Shaham, Givat-Ada, Israel) and each pot contained one plant. From here on, this growing medium will be referred to as "soil". Each pot was placed in a plastic container (13×21.5×31.5 cm; height×width×length) through a hole in its top cover. The soil surface and containers were covered with aluminum foil to avoid evaporation. A soil moisture sensor (5TE; Decagon Devices, USA) was placed in each pot. Specific coefficients of the Topp's third-order polynomial equation (Topp et al., 1980) were determined by the calibration of the sensors.

In the well-irrigated treatment, the containers were filled with water daily to ensure water availability throughout the day and avoid the need for any supplemental irrigation during the day that would induce weight Water was not supplied in the drought treatment. A drainage hole in each container kept the water level in the container after each watering at 2 cm above the pot base. Excess irrigation was intended to prevent any accumulation of salt in the soil. This setup ensured that the container weight decreased monotonically over the course of the day solely due to plant transpiration. A commercial fertilizer solution (Super Grow 6-6-6+3; Hortical, Kadima, Israel) was applied daily at 0.2% (v/v) with the irrigation water (fertigation).

Six wet wicks were placed on six additional load cells whose output provided a reference for the effect of the ambient conditions on transpiration. Each wick was a woven floor rag the lower part of which was submerged in water. The temperature and relative humidity in the greenhouse and the photosynthetically active radiation (PAR) were monitored using sensors (HC2-53-L; Rotronic, Switzerland and LI-COR 190 Quantum Sensor; LI-COR, USA).

The weighing lysimeters, soil moisture sensors and environmental sensors were connected a to CR1000 data logger trough AM16/32B multiplexers (Campbell Scientific, USA). Readings of the weighing lysimeters and the environmental sensors were taken every 15 seconds and averages for each 3-min period were stored in a data logger for further analysis. Soil moisture was measured every 3 min.

This study included two lines of tomato plants (*Solanum lycopersicum*), MP1 and M82, which exhibit anisohydric and isohydric behaviors, respectively. Each experiment consisted of three stages. During the first stage, referred to as pretreatment, the plants were irrigated daily (see details above). During the second stage, referred to as the drought treatment, irrigation was discontinued. During the third stage, referred to as the recovery treatment, daily irrigation was resumed. After all of these stages had been completed, the plant shoots were removed and weighed and the leaf area for each shoot was measured (LI-COR 3100 Area Meter; LI-COR, USA).

Leaf water potential ($\Psi_{leaf}$) (Arimad 3000 Pressure Chamber; MRC, Israel) and relative water content (RWC) were measured simultaneously on three different days during the drought treatment. Each of the measurements included five plants from each line that had been subjected to similar SWC levels (~80%, ~50% and ~20%). The measurement data was collected at 6 am, 10 am and 2 pm on days when the water content in the pots reached the specified SWC levels. Measurement data were collected from a single leaf from each plant. RWC was evaluated using the protocol described in Sade et al. (2009).

Plant daily transpiration (PDT) was calculated based on the difference between the load cell readings before dawn ($W_m$) and in the evening ($W_e$). $W_m$ and $W_e$ were calculated as the average weight over a 30-min period. The daily plant weight gain ($\Delta PW_k$) was determined based on the difference between the container weight ($W_{k+1} - W_k$) on the morning the two consecutive days, k+1 and k, respectively, when the drainage from the container following an irrigation event had finished. Note that since drainage was controlled by a hole in the wall of the container, the observed weight difference was determined solely by the plant weight gain.

Instead of evaluating the plant's physiological water-use efficiency (the ratio between accumulated $CO_2$ molecules and evaporated $H_2O$ molecules), agronomic water-use efficiency (WUE) was evaluated, defined as the ratio between the plant weight gain (APW) and the amount of water transpired. The WUE of each line was determined by fitting a linear curve for the cumulative plant weight gain during the pretreatment stage vs. cumulative water transpiration. The daily plant weight gain over the course of the drought treatment was calculated using Equation 2.1, below in which WUE is the slope of the fitted linear curve for each line.

$$\Delta PW = PDT \cdot WUE \tag{2.1}$$

The leaf area ratio (LAR), defined as the ratio between the leaf area (LA) and shoot weight at the end of the experiment, was calculated for each plant and averaged for the different lines. The shoot-weight ratio (SWR), defined as the ratio between the measured shoot weight and the calculated plant weight at the end of the experiment, was also calculated for the different plant (SWR=0.6 for both lines). Leaf area (in $cm^2$) was estimated using Equation 2.2, below.

$$LA = PW * SWR * LAR \tag{2.2}$$

The whole-plant transpiration rate [ET (g/h)] is the negative value of the first time derivative of the weight decrease during the daytime. A numerical derivative of the weight data is noisy and a data-smoothing procedure should be performed before the derivative is calculated. The Savitzki-Golay (1964) method was used for this purpose (Wallach et al., 2010). The root uptake rate, $j_r$, was determined by multiplying the first derivative of the smoothed SWR data (determined using the same procedure used for the pot-weight data) by the volume of the growing media in the pot. Change in plant RWC is induced by a difference between water influx (root uptake) and water out-flux (transpiration) over a predetermined time period. The momentary whole-plant RWC change (ARWC) is the sum of RWC changes, starting from midnight (n=0; RWC=100%) divided by plant weight. In Equation 2.3 (shown below), $\Delta t$ is the time interval between sampling events (0.05 h) and PW is the plant weight on a particular day.

$$1 - RWC_n = \Delta RWC_n = \frac{\sum_{n=0}^{n}(Jr_n - ET_n) * \Delta t}{PW} \quad (2.3)$$

The vapor pressure deficit (VPD) is the difference (in KPa) between the vapor pressure of the saturated air and the vapor pressure of the ambient air. In plants, this refers to the difference between the pressure in the substomatal cavities and the atmospheric pressure. In Equation 4 (shown below), T is the air temperature (° C.), RH is relative humidity (0-1), 0.611 is the saturation vapor pressure at 0° C. and 17.502 and 240.97 are constants (Buck, 1981).

$$VPD = (1 - RH)0.611e^{\left(\frac{17.502 * T}{240.97 + T}\right)} \quad (2.4)$$

The transpiration rate normalized to the plant leaf area (E [mmol sec$^{-1}$ m$^{-2}$] is equivalent to the common values measured by the gas-exchange devices, but refers to the whole plant, not only the small area measured by the devices. The canopy vapor conductance (gs$_c$ [mmol sec$^{-1}$ m$^{-2}$]) can be calculated using Equation 2.5, in which P$_{atm}$ is the atmospheric pressure (101.3 KPa).

$$gsc = \frac{E * P_{atm}}{VPD} \quad (2.5)$$

The characteristic curve of the relationship between $\Psi(\theta)$, where $\Psi$ is the soil matrix potential and $\theta$ is the SWC, and the soil hydraulic conductivity function, $K(\theta)$, was calculated by fitting the van Genuchten model (Van-Genuchten, 1980) to the collected $\Psi(\theta)$ data.

TABLE 1

The van Genuchten model parameters for the growing medium used in this study

| Parameter | n | m | α | $_s\theta$ | $_r\theta$ | K$_s$ (cm/h) |
|---|---|---|---|---|---|---|
| Value | 2.238 | 1 − 1/n | 0.036 | 0.8 | 0.05 | 4.9 |

* The retention curve was constructed based on five samples and the model was fit to the mean.

Plant Hydraulic Conductivity

In general, the whole-plant hydraulic conductivity is equal to transpiration (E, normalized to leaf area) divided by the potential difference between the leaf ($\Psi_{leaf}$) and the root. Root potential was not measured in this study, so we assumed that the leaf water potential before dawn ($\Psi_{PD}$) was in equilibrium with the root potential (Holloway-Phillips and Brodribb, 2011). Therefore, the whole-plant hydraulic conductivity (K$_{plant}$) was calculated using Equation 2.6, below:

$$E_{plant} = \frac{E}{\psi_{PD} - \psi_{leaf}} \quad (2.6)$$

Transpiration vs. Soil Water Content

Comparing the behavior of different plants over time may lead to erroneous conclusions, as the plants' intrinsic parameters are not compared at similar levels of water availability. At a certain time, plants that transpire more than others will face lower SWC levels. For this reason, the plants' transpiration (E) was plotted versus SWC ($\theta$). The daily E and $\theta$ values presented are the average values observed between 11 am and 1 pm. Equation 2.7 was used to fit to the E($\theta$) data for each tomato line. In Equation 2.7, E$_{max}$, b and $\theta_{cr}$ are the model-fitting parameters.

$$E(\theta) = \begin{cases} E_{max}; & \theta \geq \theta_{cr} \\ E_{max} + b(\theta - \theta_{cr}); & \theta < \theta_{cr} \end{cases} \quad (2.7)$$

Data Analysis

All of the data analysis was performed using Matlab software (MathWorks, USA). The data set included daily data (one value per day for each plant) and continuous data calculated every 3 min (480 values per day for each plant). Means that were deemed significantly different at P<0.05 were compared using Student's t-test and one-way ANOVA (noted in the figure legends). Comparisons of the parameters of Equation 2.7 for the two lines were made using the 95% confidence intervals. Non-overlapping confidence intervals indicate a significant difference at P<0.05.

Stomatal Aperture and Density

Abaxial leaf stomata were imprinted on glass as detailed in (Geisler and Sack, 2002). All samples were collected at the summer experiment around 11 am. The stomata were counted and photographed under a bright-field inverted microscope (Zeiss 1M7100; Zeiss, Jena, Germany) on which a Hitachi (Hitachi; Japan) HV-D30 CCD camera had been mounted. Stomatal images were later analyzed to determine aperture size, using the ImageJ software area-measurement tool. A microscopic ruler (Olympus; Tokyo, Japan) was used for the size calibration.

Quantitative Analysis of Gene Expression by Quantitative PCR (PCR)

Tomato leaves for this analysis were harvested at the same time as other leaves were harvested for the measurements of RWC and leaf water potential (see "Experimental Setup" above). Total RNA was extracted using Tri-Reagent (Molecular Research Center, USA) and treated with RNase-free DNase (Fermentas, Vilnius, Lithuania). cDNA was prepared using the EZ-First Strand cDNA Synthesis Kit (Biological Industries, Israel) according to the manufacturer's instructions. qPCR was performed in the presence of SYBR Green I (Takara, Japan) in a Corbett Research Rotor-Gene 6000 Cycler. The tomato β-actin gene (Sade et al., 2012) was used as a reference for the standardization of the amounts of cDNA. The reaction procedure was as follows: 30 s at 94° C., followed by 40 cycles consisting of 10 s at 94° C., 30 s at 60° C., and then another 20 s at 72° C. The primer pairs used to amplify specific fragments are listed in Table 2, below.

TABLE 2

| Target gene | Primer sequence | Seq ID | Accession no. |
|---|---|---|---|
| β-actin | 5' GGAAAAGCTTGCCTATGTGG 3' | 1 | TC198350 |
| | 5' CCTGCAGCTTCCATACCAAT 3' | 2 | (Sade et al., 2012) |
| TIP1-1 | 5' GGGTTCTGGTATGGCTTTCA 3' | 3 | TC170408 |
| | 5' TGTTTCCACCAACAAAAGCA 3' | 4 | Sade et al., 2009 |

TABLE 2-continued

| Target gene | Primer sequence | Seq ID | Accession no. |
|---|---|---|---|
| TIP2;2 | 5' ATGGCTGGCGGCGTAGCTATT3' | 5 | TC186503 |
|  | 5' AGAGCAAATCCATGGCAAAC 3' | 6 | Sade et al., 2009 |
| TIP1-2 | 5' AGTAAGAAACAATAATGCCAATTTC 3' | 7 | TC178388 |
|  | 5' AAAAGAACTCAGCTGTTGCAG 3' | 8 | Sade et al., 2009 |
| TIP3-1 | 5' GCTCATGATGAAGCTCCAGTT 3' | 9 | TC179273 |
|  | 5' GGCCTCTTAAGAAAGCAAACAA 3' | 10 | Sade et al., 2009 |
| PIP1;5 | 5' GTGAAGGGCTTCATGGTAGG 3' | 11 | TC178447 |
|  | 5' GGAAGTGGTGCCAAAATAGG 3' | 12 | Sade et al., 2009 |
| TIP4-1 | 5' GGTCTCATGTTCCTCTTCCAA 3' | 13 | TC184148 |
|  | 5' CATGACCAAACGGGGTAGTT 3' | 14 | Sade et al., 2009 |
| TIP2-3 | 5'CTATGAACCCAGCACGATCA 3' | 15 | TC170459 |
|  | 5'CTGAGGTTGGAAGTGGTGTG3' | 16 | Sade et al., 2009 |
| PIP2-5 | 5' GGGTGGTGGTGCTAATGAAC 3' | 17 | TC184369 |
|  | 5' TTGGAAGTGGTGCCAATACA 3' | 18 | Sade et al., 2009 |

Results

Comparison of Daily Transpiration Rates of Multiple Plants

Figure 20A:
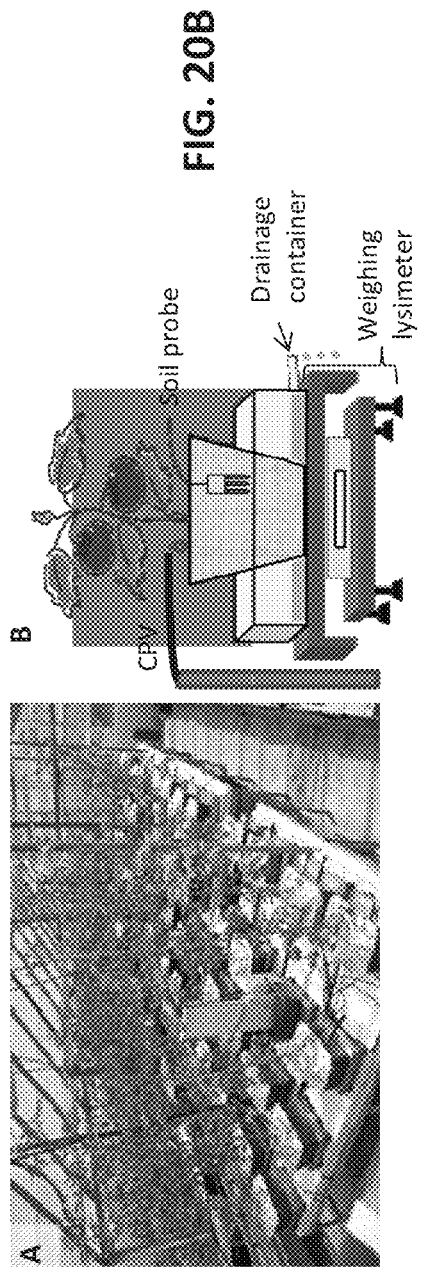
FIGS. 20A-C show lysimeter system and full treatment profile regime. (A) The prototype greenhouse array (consisting of 48 weighing lysimeters) loaded with MP1 and M82 tomato plants. This fully automated system collects data from all of the plants simultaneously. (B) Drawing of a single unit composed of a 3.9-L pot that was inserted into an opaque plastic drainage container through an opening in the top of the container. The pot-container system sits on a sensitive, temperature-compensated load cell. The purpose of the drainage container is to keep water available to the plant (0-600 mL) throughout the day to avoid weight changes caused by daytime irrigation events, which would complicate the calculation of the continuous momentary transpiration rate. A soil probe in each pot continuously monitors the volumetric water content and electrical conductivity of the growth media. The irrigation system is controlled by preprogrammed valves (CPV). An algorithm for plant-specific multiple physiological analyses was developed to provide the (C) mean variation in weight and SE in the different tested lines throughout the full-irrigation, drought and recovery periods.
Figure 20B:
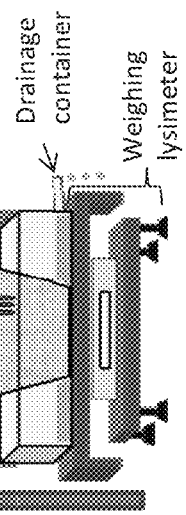
Figure 20C:
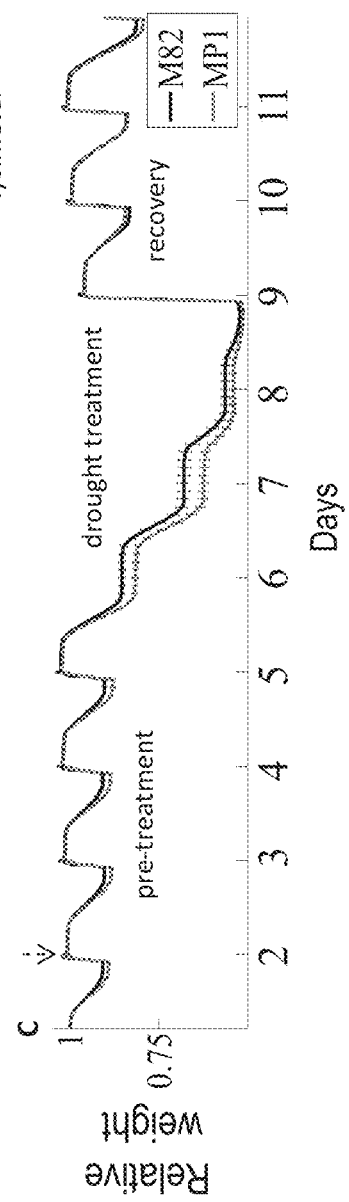

Two closely related tomato lines, M82 and MP1, were used in this work since (according to our previously collected, unpublished data) these lines exhibit isohydric and anisohydric behaviors, respectively. A comparable set of criteria and parameters that enable us to emphasize the physiological differences between different whole-plant water-regulation behaviors under specific ambient conditions were first defined using a novel high-throughput whole-plant diagnostic system (see Materials and Methods and FIGS. 20A-C).

Observations of whole-plant transpiration rates (E) and canopy vapor conductance ($gs_c$) across a broad range of SWC (θ) levels (FIGS. 13A-E) revealed that the E and $gs_c$ of MP1 were consistently higher than those of the M82 line. The plot of E versus θ (FIGS. 14A-C) was found to provide more physiological relevance for comparisons of the transpiration regulation of different plants than a plot of E over time. Using θ as the basis for comparisons of plant transpiration behaviors is justified by the fact that plants that transpire more reduce the SWC more quickly and are sooner faced with water shortages.

MP1 Exhibits a More Variable Transpiration to Soil Water Content Ratio

The plot of E over θ (FIGS. 14A-C) revealed a consistent midday transpiration level ($E_{max}$) for the given ambient conditions down to the critical SWC level ($θ_{cr}$) and E diminished sharply as θ decreased further. Such E to θ variation indicates that soil water availability is a limiting factor only when $θ<θ_{cr}$; whereas atmospheric water demand controls E when the SWC is greater than the critical level ($θ>θ_{cr}$). MP1's E to θ ratio was consistently higher than that of M82 across the range of examined θ levels and light conditions as we measure in both the summer (FIG. 14A) and winter experiments (FIGS. 14A-C; The level of natural irradiance was lower during the winter; whereas artificial means were used to keep VPD at similar levels in the different seasons FIG. 21A and FIG. 13A).

When sufficient water is available in the soil, the ability of a plant to convey water is related to many physiological, morphological and anatomical characteristics, which together determine the $E_{max}$ of an individual plant. A comparison of the stomatal densities and apertures of these closely related tomato lines revealed similar stomatal densities (24±3 and 21.3±1.3, stomata per 0.1 $mm^2$ for MP1 and M82, respectively, mean±SE, MP1 n=at least 16 leaves) for the two lines and that the stomatal apertures of MP1 were wider than those of M82 (45.5±1.6 $μm^2$ and 25.2±2 $μm^2$, respectively, mean±SE, n=at least 16 leaves) in the presence of similar soil-to-atmosphere water potential differences. Therefore, one may conclude that M82 exhibits more conservative water-balance management behavior than MP1. This difference may reflect differential sensitivity of the stomatal response to similar leaf-water statuses or the use of different mechanisms for the regulation of leaf water status (LWS).

Differences in the Regulation of Leaf Water Status in Anisohydric and Isohydric Plants We monitored the relations between the calculated $gs_c$, leaf RWC and $Ψ_{leaf}$ under similar atmospheric conditions at three different SWC levels (FIGS. 15A-C). In the summer, at full soil water availability, the two lines showed a similar daily pattern of $gs_c$ variation, namely, a peak at ~8 am, followed by a decline through ~1 pm and a leveling out later in the day. The leaf RWC and $Ψ_{leaf}$ of both lines declined until ~10 am and leveled out afterward. While no differences were noted between the leaf RWC patterns of the two lines, MP1 plants reached lower $Ψ_{leaf}$ values than M82 before noon (FIGS. 15A-C, left column).

Under conditions of moderate soil water availability (40-50%, just below $θ_{cr}$), the rate of $gs_c$ increased gradually in both lines, reached a peak at ~9 am and then decreased moderately throughout the rest of the day. MP1 plants maintained higher $gs_c$ values throughout the morning hours, but the difference between the two lines vanished during the afternoon. Both lines leaf RWC patterns were similar to those observed in the well-irrigated treatment (i.e., rapid reduction in the morning and stabilization at ~10 am). Yet, while the RWC levels observed in M82 in this treatment at midday were similar to those observed in the well-irrigated treatment, the RWC levels of the MP1 plants in this treatment were significantly lower (~6%) than those observed in the well-irrigated treatment. $Ψ_{leaf}$, on the other hand, decreased monotonically during the daytime hours in both lines, with higher values observed for M82. The difference between the two lines was significant throughout the day (FIGS. 15A-C, middle column).

Figure 22:
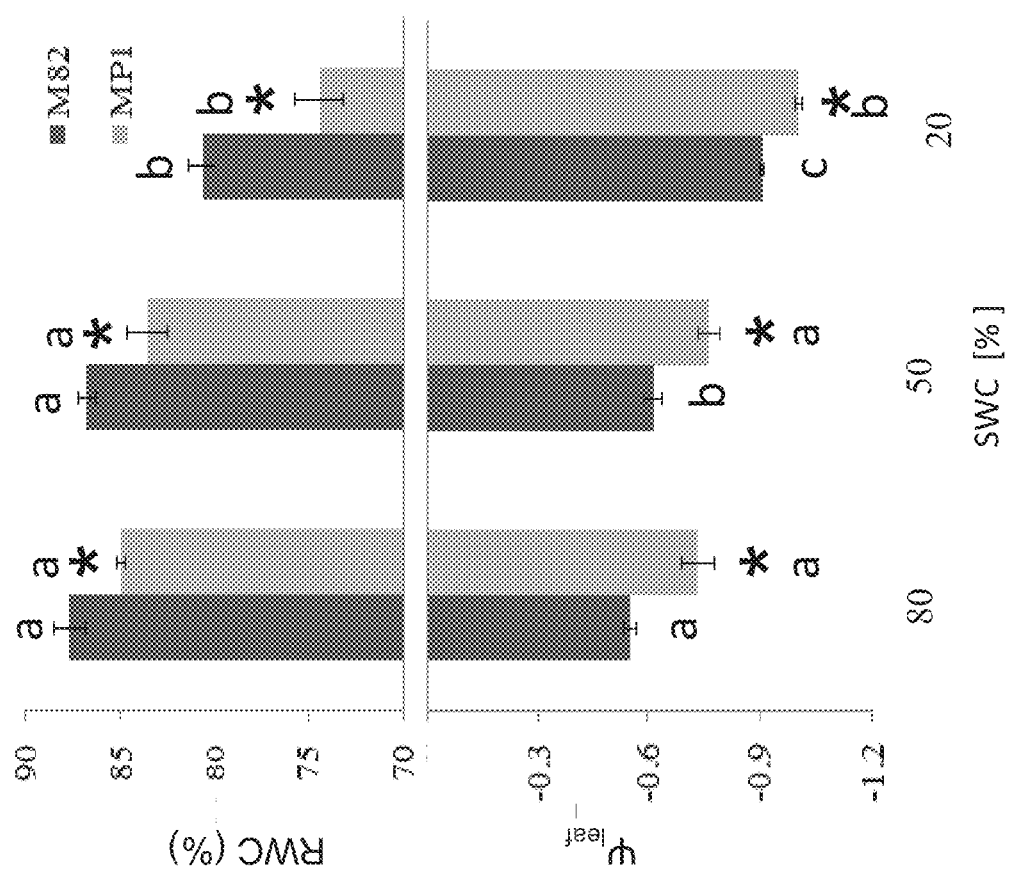
FIG. 22 shows relationship between leaf RWC and $\Psi_{leaf}$ at different SWC levels in the winter experiment. Plants were grown on the lysimeter system and SWC was monitored continuously. When predefined values of SWC=70-80%, SWC=40-50% (around $\theta_{cr}$), and SWC=10-20% were observed, leaves were harvested from the plants and their midday (A) RWC and (B) $\Psi_{leaf}$ were measured. Each column is the mean±SE of 9 leaves from 3 to 5 different plants whose pots reached the exact SWC at the time of the measurement. Asterisks indicate significant differences (Student's t-test, p<0.05) between the lines in a treatment. Different letters represent significant differences [one-way analysis of variance (ANOVA) test, P<0.05] between midday measurements of the same line in the different treatments.

At the lowest SWC level (10-20%), no differences were detected between the $gs_c$ rates of the two lines, which were each very low. The $\Psi_{leaf}$ values continued to decrease as SWC decreased, but there was no significant difference between the midday $\Psi_{leaf}$ values of the two lines. Nevertheless, the RWC values of M82 were significantly higher than those observed for MP1; the water content of MP1 under these conditions was ~22% lower than under normal irrigation conditions (FIGS. 15A-C, right column). These results (confirmed in winter experiments, see FIG. 22) demonstrate that MPI employs a more anisohydric regulation strategy than M82.

Differences in Whole-Plant Water Regulation in Anisohydric and Isohydric Plants

Figures 16A, 16B, 16C:
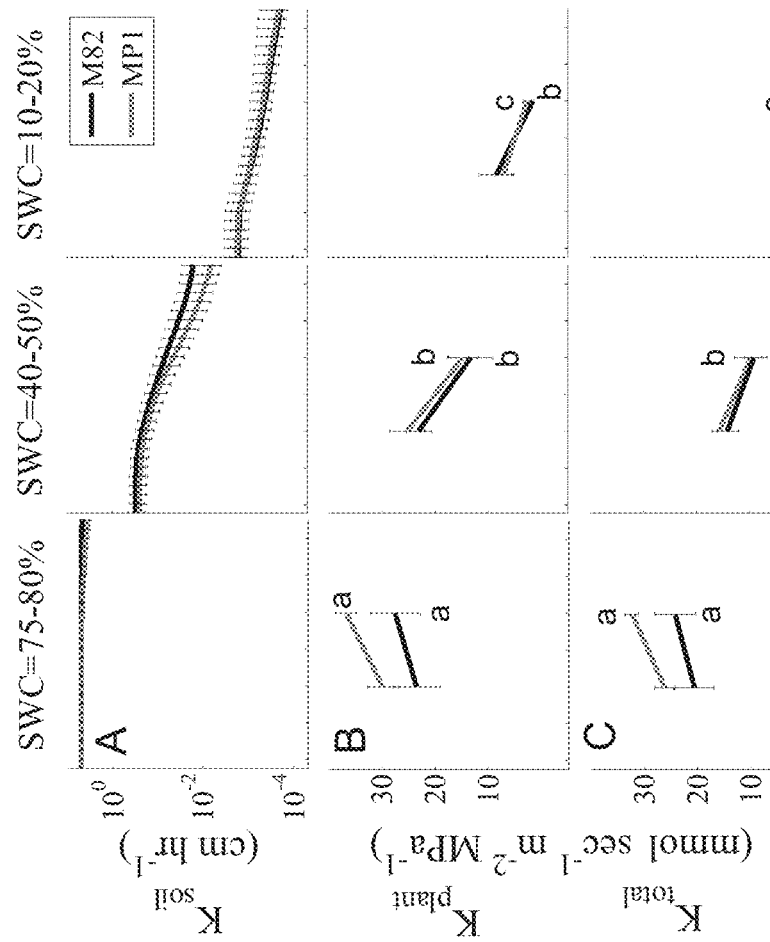
FIGS. 16A-C show hydraulic conductivity of different components of the system at different SWC levels. (A) Soil hydraulic conductivity ($K_{soil}$), (B) whole-plant hydraulic conductance ($K_{plant}$) and (C) conductance of the soil-plant continuum ($K_{total}$). Each point is the mean±SE of 5 plants of each line. Different letters represent significant differences [one-way analysis of variance (ANOVA) test, P<0.05] between midday measurements of the same line in the different treatments.

Interestingly, RWC was the most conserved element of the leaf water status. Moreover, the fact that MP1 maintained a higher level of transpiration under well-irrigated conditions with no reduction in its RWC, in contrast to M82, suggests that the MP1 plants had higher levels of plant water conductance ($K_{plant}$). Measurement of the SWC allows us to evaluate the soil matrix potential and the soil's hydraulic conductivity ($K_{soil}$; FIG. 16A). Together with the leaf water potential (see Material and Methods) and the momentary transpiration rate (Equation 2.6), these data can be used to evaluate the plant hydraulic conductance ($K_{plant}$; FIG. 16B). Under well-irrigated conditions, $K_{soil}$ did not reduce $K_{plant}$, which remained high. The midday $K_{plant}$ of MPI decreased more quickly than that of M82, resulting in a greater decrease in $K_{plant}$ of MP1 as SWC decreased. The combined conductivity of the two hydraulic systems (following the adjustment of units) is the hydraulic conductivity of the soil-plant system, referred to as $K_{total}$ (FIG. 16C).

Figures 17A, 17B, 17C:
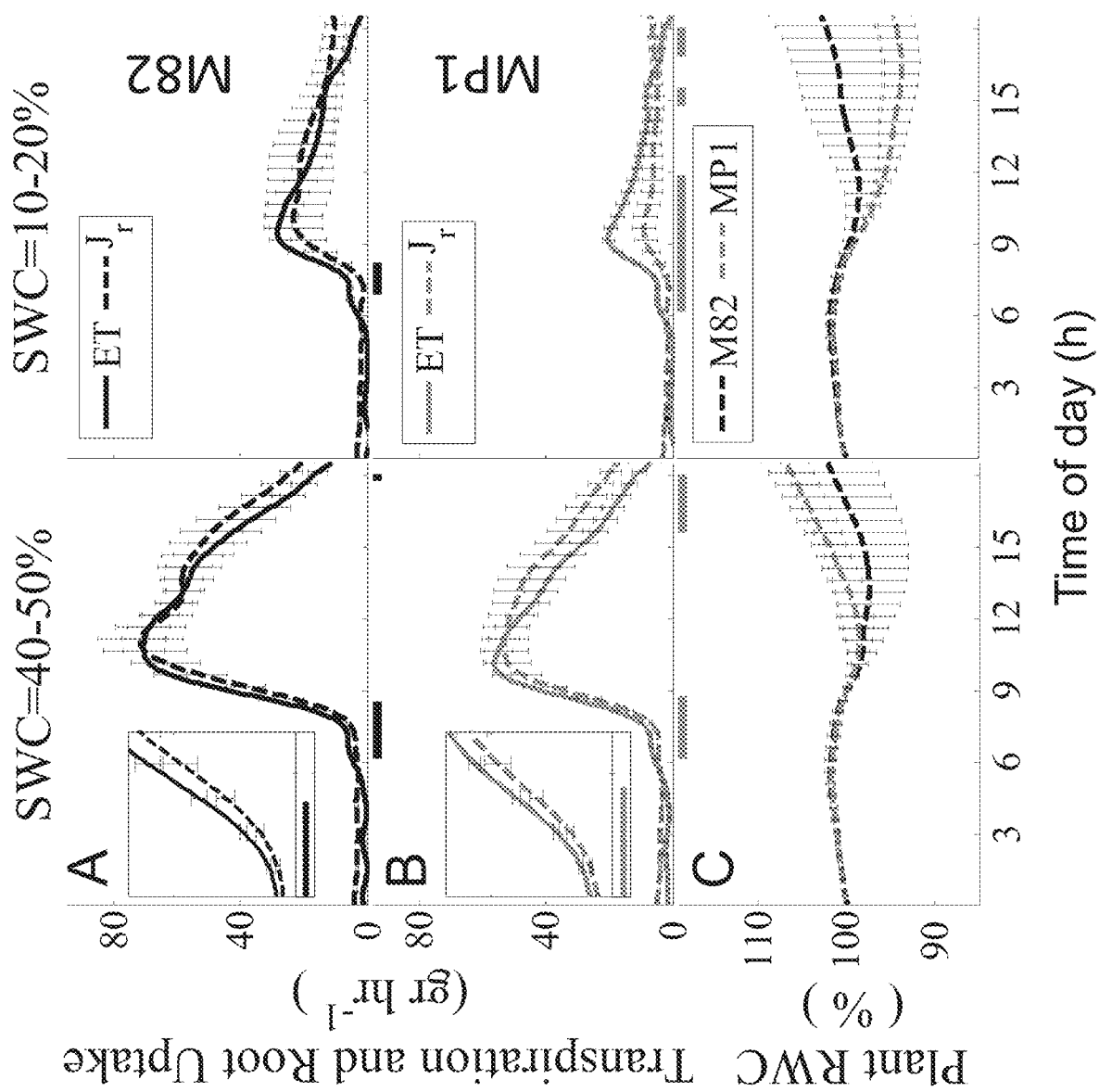
FIGS. 17A-C show daily water influx and out-flux and whole-plant water balance at different SWC levels. Daily pattern of the rate of plant water loss (ET) and the rate of root water uptake ($J_r$) measured simultaneously for (A) M82 and (B) MP1. The cumulative difference between the influx and the outflux is the change in the (C) whole-plant relative water content (RWC). Each data point is the mean±SE of at least 9 plants of each line. Lines under the slopes indicate a significant difference (Student's t-test, p<0.05 were done every 30 min) between the transpiration rate and the rate at which water was taken up by the roots. Insets show the magnitudes of the slopes between 7 and 9:30 am.

The fact that MP1 plants maintained higher transpiration rates than M82 plants as $K_{soil}$ decreased, leading to a sharper decrease in $K_{plant}$ in MP1, suggests that these two lines differ in their patterns of shoot-to-root coordination of water-balance regulation. The whole-plant water balance can be evaluated by comparing the flow of water into the roots root ($J_{root}$) with the flow of water out of the canopy (ET; FIGS. 17A-C). $J_{root}$ is determined by continuously measuring SWC (using soil probes) and ET is evaluated by the simultaneous continuous measurement of plant weight (see Materials and Methods). No difference between the two fluxes indicates a consistent whole-plant RWC; whereas a deviation between the two fluxes indicates that the whole-plant RWC is either decreasing or increasing (FIG. 17C; Materials and Methods). The daily pattern of the RWC data collected from the MP1 plants reveals that, under severe stress, this line experiences considerably greater water loss than M82; this observation is congruent with our manual leaf RWC measurements.

In general, in both lines, during the early morning, more water flows out of the plant than flows into the plant. This is followed by a flux equilibrium in the late morning that persists through midday and greater influx than out-flux during the afternoon.

TIP and PIP Expression Patterns in Anisohydric and Isohydric Plants in the Presence of Different Soil Water Content Levels While this pattern of shoot-root coordination was observed in M82 even in drier soils, MP1 plants exhibited much less root-shoot synchronization, allowing for much greater out-flux than uptake. This flux-balance evaluation is congruent with the lower RWC values measured in the MP1 plants (FIGS. 15A-C and FIGS. 17A-C).

Figures 18A, 18B, 18C:
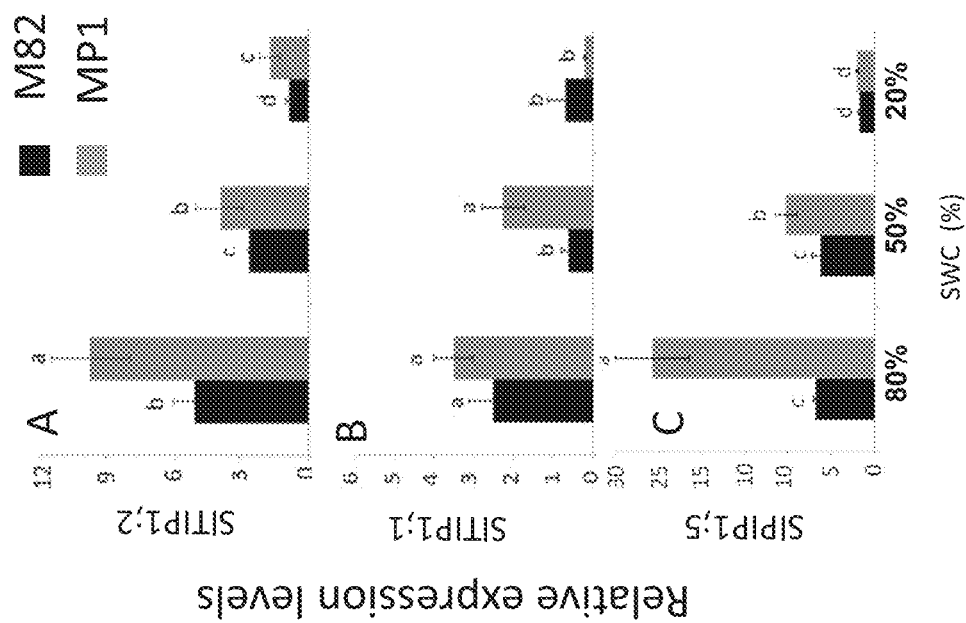
FIGS. 18A-C show relative expression profiles of SlTIP1; 1, SlTIP1;2, and SlPIP1;5 in M82 and MP1 at the different SWC levels. qPCR analysis of the relative expression of (A) SlTIP1;2, (B) SlTIP2;1 and (C) SlPIP1;5 in MP1 (gray bar) and M82 (black bar) under different SWC conditions (~80%, ~50%, ~20%). Data are presented as means±SE (N=5). Different letters above the columns represent significant differences (t-test, P<0.05).

Plasma membrane intrinsic proteins, PIP AQPs, are known to control the osmotic permeability of cells and plants' hydraulic conductance. Tonoplast AQPs, TIPs, have been shown to regulate plant RWC and isohydric behavior, suggesting that AQPs might be involved in the cellular mechanism responsible for the difference in the water-balance regulation of these two tomato lines. When we compared the expression levels of several TIPs and PIPs in MP1 and M82 leaves collected from the three SWC treatments, we found that two TIPs and one PIP were expressed at significantly higher levels in MP1 than in M82, under both intense and moderate drought conditions (FIGS. 18A-C). Four more TIPs and one more PIP, whose expression levels did not differ between the two lines or decrease in response to drought conditions, were assumed to have smaller effects on the osmotic water permeability and hydraulic profiles of the two lines (FIGS. 23A-E).

DISCUSSION

In the presence of high VPD, leaves are at risk of dehydrating if the amount of water they are losing through transpiration is greater than the amount of water they are receiving through the stem. The fine regulation of transpiration depends on many control points along the soil-plant-atmosphere continuum (SPAC). Slight changes in the sensitivity of different elements along the SPAC can lead to the use of different water-balance management strategies, which will be reflected in the plant's rate of transpiration (Monteith, 1965; Farquhar and Wong, 1984; Franks et al., 1997; Feddes and Raats 2004; Buckley, 2005). In the present example, the variation in the transpiration rates of the plants in the different treatments was monitored.

The comparison between the isohydric tomato line M82 and the anisohydric tomato line MP1, which have similar stomatal densities, revealed significant differences in the whole-plant E and $gs_c$ regulation mechanisms used by these two lines. Thus, these tomato lines served as good model plants for isolating the leaf status vs. ambient threshold signal that distinguishes isohydric behavior from anisohydric behavior.

Relationship Between Transpiration and Soil Water Content

Figures 13A, 13B, 13C, 13D, 13E:
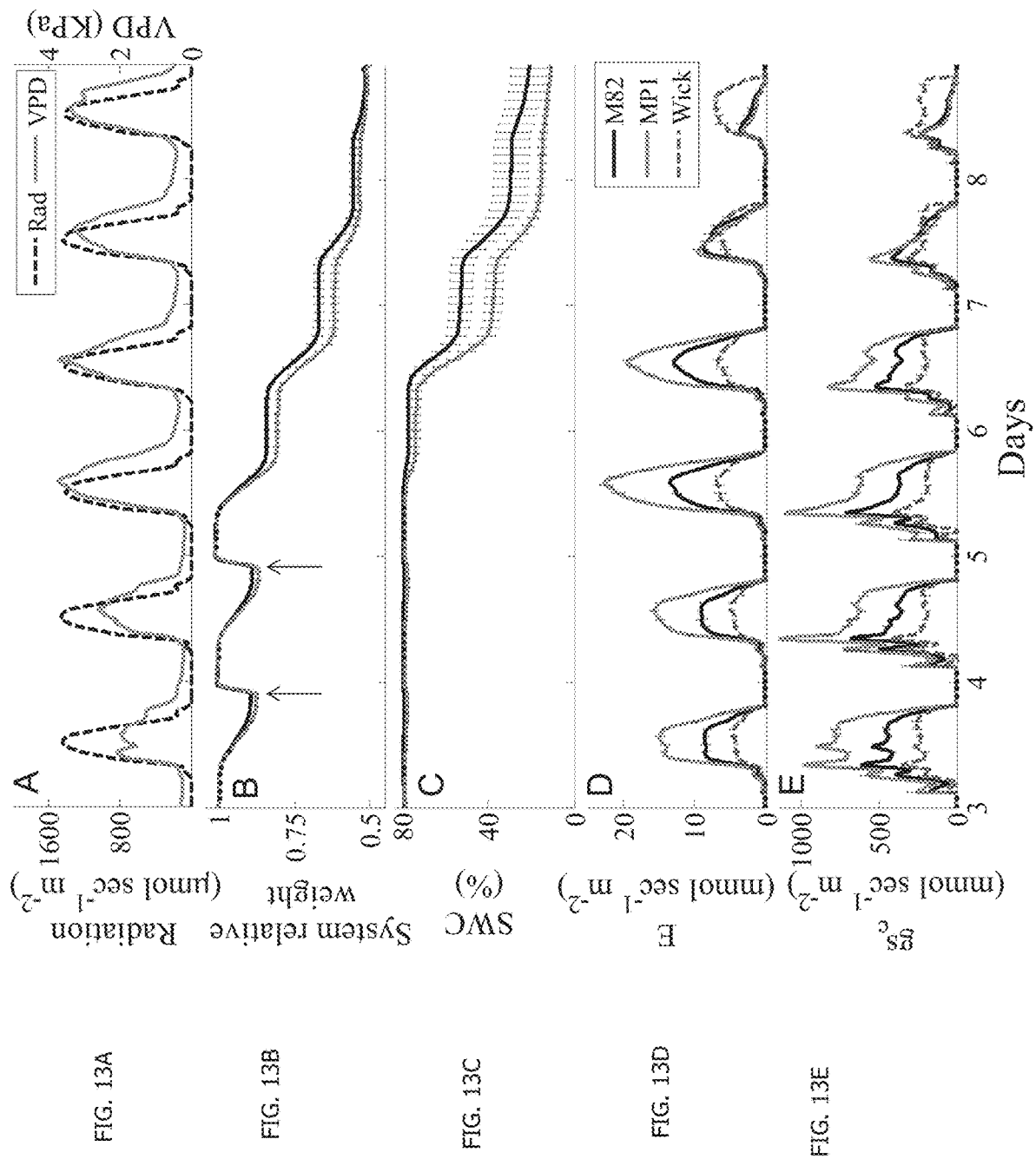
FIGS. 13A-E show variation in different whole-plant parameters along a soil-atmosphere water gradient. (A) Daily VPD and radiation (Rad) over the 6 consecutive days of the experiment, which included 3 days of full irrigation followed by 3 days of drought. (B) Variation in the weights of the M82 and MP1 plants (relative to the initial weights of these plants) over the course of the full-irrigation and drought treatments. The observed weight increase (marked by arrows) was the result of irrigating up to the level of the drainage hole (FIG. 20B). (C) Variation in SWC over the 6 days of the experiment. (D) Whole-plant transpiration E [mmole $m^{-2}$ $s^{-1}$] over the course of the experiment. To eliminate the effect of plant size on transpiration rate, we normalized the rate of plant water loss to the leaf surface area. (E) The whole-plant canopy vapor conductance $gs_c$ [mmole $m^{-2}$ $s^{-1}$] was calculated as the ratio of E to the simultaneously calculated VPD. Each curve (B-E) is the mean of 9 to 11 plants of each line; SE was calculated every 90 min.
Figures 14A, 14B, 14C:
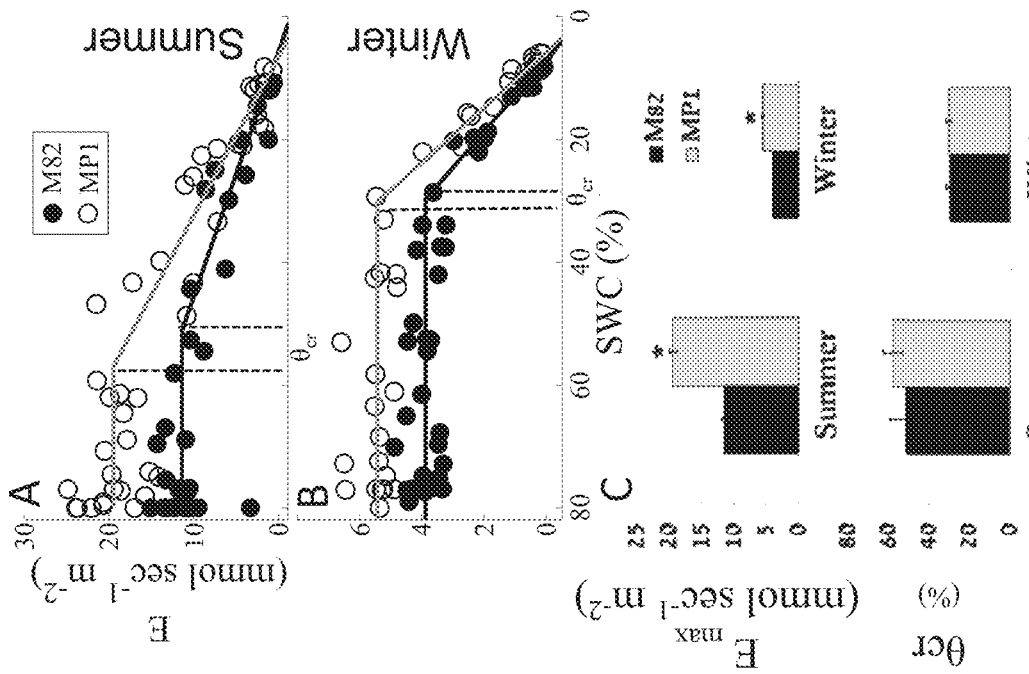
FIGS. 14A-C show midday transpiration vs. SWC. Midday whole-plant transpiration as a function of SWC over the entire period of the (A) summer experiment (same plants as in FIGS. 1A-1B) and (B) winter experiment (n=11 for MP, n=9 for M82, see FIG. 21A for a description of the ambient conditions). (C) The mean (±SE) of the maximum daily transpiration rate ($E_{max}$) and the mean (±SE) critical SWC ($\theta_{cr}$). Asterisks indicate non-overlapping 95% confidence intervals.

Questions concerning the leaf internal "closing" signals, how those signals are transferred through the guard cells and what characterizes the different controlling behaviors remain unanswered (Buckley, 2005). The results in the present example revealed similar E and $gs_c$ patterns in both lines, with different sensitivity to ambient signals (FIGS. 13A-E). Yet, in order to reveal the biological mechanisms that regulate these processes, it is desired to eliminate or reduce the environmental disparities associated with soil water variation over the course of the experiment. Accordingly, instead of evaluating the E over time for the two lines, the midday E values were compared with the SWC levels (FIGS. 14A-C). The fact that MP1 maintained E levels that were higher than those of M82 at similar SWC levels, regardless of the ambient conditions (winter or summer) suggests that the differences observed between the lines stem mainly from differences in biological regulation rather than from differences in soil water availability. The substantial increase in the $E_{max}$ values of both lines during the summer may have been the result of direct sensitivity to some atmospheric parameters, such as radiation intensity and/or VPD. The common understanding is that guard cells do not sense relative humidity or VPD (Mott et al., 1999) and that stomatal closure observed in response to an increase in VPD is an indirect response to changes in the leaf water status (Farquhar, 1978; Mott and Franks, 2001; Buckley, 2005). On the other hand, the response of stomatal aperture to light is well known.

Figures 21A, 21B, 21C, 21D:
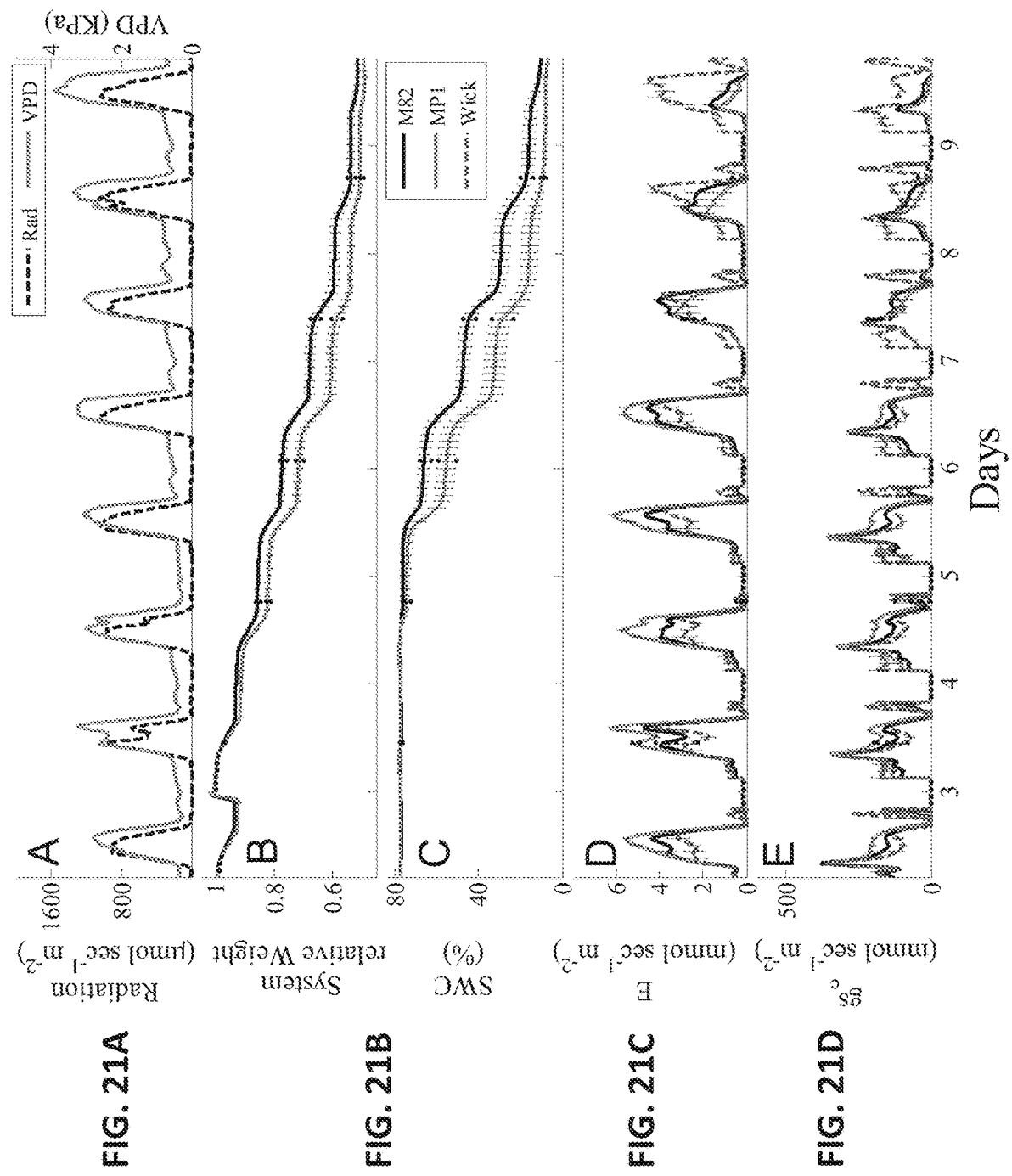
FIGS. 21A-D show whole-plant transpiration regulation in response to the soil-atmosphere water gradient (winter experiment). (A) Daily VPD and radiation (Rad) during the 8 consecutive days of the experiment, which included 2 days of full irrigation, followed by 5 days of drought. (B) Relative variation in the weights of the M82 and MP1 plants over the course of the full-irrigation and drought treatments, as compared to their initial weights. The weight of the pots increased from the start of irrigation until the water reached the drainage hole (see also FIG. 20B). (C) Soil water content (SWC) during these stages. To eliminate the effect of plant size on transpiration rate, which might be related to the faster weight loss and faster decrease in SWC observed among the MP1 plants, the rate of plant water loss was normalized to leaf surface area. (D) Whole-plant transpiration E [mmole $m^{-2}$ $s^{-1}$] and (E) whole-plant canopy vapor conductance ($gs_c$ [mmole $m^{-2}$ $s^{-1}$] were calculated as the ratio of E to the simultaneously measured VPD. As expected, the submerged-wick control treatment showed near constant water loss throughout the experiment. Each curve (B-E) is the mean of 9 M82 plants or 11 MP1 plants. SE values were calculated every 90 min.

Repeating the experiments under similar VPD conditions, but substantially different light conditions (summer and winter; FIG. 13A and FIG. 21A) revealed that radiation intensity strongly affects $E_{max}$ in both lines. An approximately 35% increase in the intensity of natural radiation during the summer experiment as compared to the winter experiment (~1400 μmol sec$^{-1}$ m$^{-2}$ vs. ~900 μmol sec$^{-1}$ m$^{-2}$, respectively) increased the $E_{max}$ and $gs_c$ of MP1 3.6-fold and the $E_{max}$ and $gs_c$ of M82 2.9-fold. Despite a similar pattern of responses to light changes, MP1 plants demonstrated greater sensitivity to this difference in radiation. Yet, while light and VPD control $E_{max}$ when water is readily available in the soil, at lower SWC levels, soil water availability becomes the limiting factor for transpiration. The gradual decrease in $E_{max}$ observed when SWC decreased below $\theta_{cr}$ indicates that soil water availability became the limiting factor for $E_{max}$ when $\theta < \theta_{cr}$, inhibiting the plant from meeting the atmospheric water demand (see the linear $E_{max}$ related to SWC, FIGS. 14A-B). Furthermore, the value of $\theta_{cr}$ depends on momentary atmospheric water demand and decreases as E decreases (as observed in the winter experiment). Interestingly, while significant differences were observed between the $E_{max}$ values of MP1 and M82, no differences were noted between the associated $\theta_{cr}$ values (FIG. 14C). This suggests that some of the water lost to transpiration comes from the plant RWC rather than from the soil (this point is discussed further below).

The Relationship Between Transpiration and Leaf Water Status

The different stomatal regulation of MP1 and M82 could be due to differential stomatal sensitivity to similar leaf water statuses or differential regulation of leaf water status under similar environmental conditions. The higher levels of E and gs observed for MP1 at similar and lower RWC and $\Psi_{leaf}$ levels (FIGS. 15A-C) suggest that this line is less sensitive than M82 to differences in these parameters.

M82 maintained its RWC better than MP1, as could be expected from an isohydric line. On the other hand, the $\Psi_{leaf}$ of M82 declined over the entire range of SWC levels. In fact, RWC decreased more slowly than $\Psi_{leaf}$ in both lines throughout the drought period (FIGS. 15A-C, FIG. 22), inconsistent with the classical definition for isohydric plants (Tardieu and Simonneau, 1998). Similar results were recently reported in a study conducted in a line of genetically modified M82 plants that were made anisohydric by increasing the permeability of their tonoplasts to water (Sade et al., 2012). A higher turgor-loss point is considered to be a drought-tolerance trait (Kramer and Boyer, 1995; McDowell, 2011; Bartlett et al., 2012). Variation in leaf water potential at a the turgor-loss point within and across species allows the maintenance of high relative water content at the turgor-loss point, as reported in a recent review (Bartlett et al., 2012), suggesting that RWC takes a higher place in the leaf water status hierarchy. In accordance with these findings, we believe that the definition of isohydric behavior should be modified to emphasize the role of RWC in leaf water status (i.e., "isohydric plants reach a constant leaf RWC at midday and maintain that level of RWC over a wider range of SWC levels than anisohydric plants").

From the Cellular Level to the Whole Plant: Mechanisms Responsible for the Differences Between Isohydric and Anisohydric Behavior The two tomato lines exhibited significantly different E and $gs_c$ levels and significantly different stomatal apertures when the SWC was high. Despite MP1's higher transpiration rate, the RWC and $\Psi_{leaf}$ levels observed for MP1 were no different that those observed for M82, most likely due to high $K_{plant}$, which supported sufficient inflow to maintain a steady-state leaf water status. However, $K_{plant}$ cannot be considered the sole parameter differentiating isohydric from anisohydric behaviors, particularly under suboptimal soil water conditions. As SWC decreased, $K_{plant}$ declined faster in MP1 than in M82 (FIG. 16B). Yet, at full water availability and under mild drought stress, MP1 maintained higher E and $gs_c$, resulting in a significant water deficit in the leaf. Even in the driest soil (10-20% water content), MP1 plants maintained a higher difference between water influx and out-flux than M82 plants (FIGS. 17A-C), leading to an even larger water deficit in the leaves of those plants.

Coping with a water deficit requires a buffering mechanism to protect the biochemical reactions proceeding in the cytoplasm. Recently, we suggested that the regulation of the osmotic water permeability of the tonoplast, via its AQPs, plays a major role in this compensating mechanism of the cytoplasm (Sade et al., 2009; Sade et al., 2012). Other studies have pointed to a similar relationship between the expression of TIPs and plant vigor and drought-stress resistance (Tyerman et al., 1999; Lin et al., 2007; Peng et al., 2007), as well as TIP and PIP expression, which were positively correlated with high gs and Kleaf (Pou et al., 2012).

Indeed, the transcript expression profiles of two TIPs revealed differential expression in leaves from MP1 and M82 leaves, including greater SlTIP1;2 expression under all conditions in MP1. In MP1, SlTIP1;1 was expressed at similar levels at high and moderate SWC levels. However, in M82, SlTIP1;1 was expressed at a significantly lower level in the 50% SWC treatment (FIG. 18B). In addition, the level of expression of a plasma membrane PIP, SlPIP1;5, in MP1 was five times that observed in M82 (FIG. 18C). Interestingly, the expression of this gene decreased rapidly as drought developed, in a pattern similar to that observed for the $K_{plant}$ of MP1. SlPIP1;5 is closely related to AtPIP1;2 (from *Arabidopsis thaliana*) and NtAQP1 (from tobacco (*Nicotiana tabacum*), which have been shown to play significant roles in the regulation of plant hydraulic conductance in those species (Sade et al., 2010).

Figure 24:
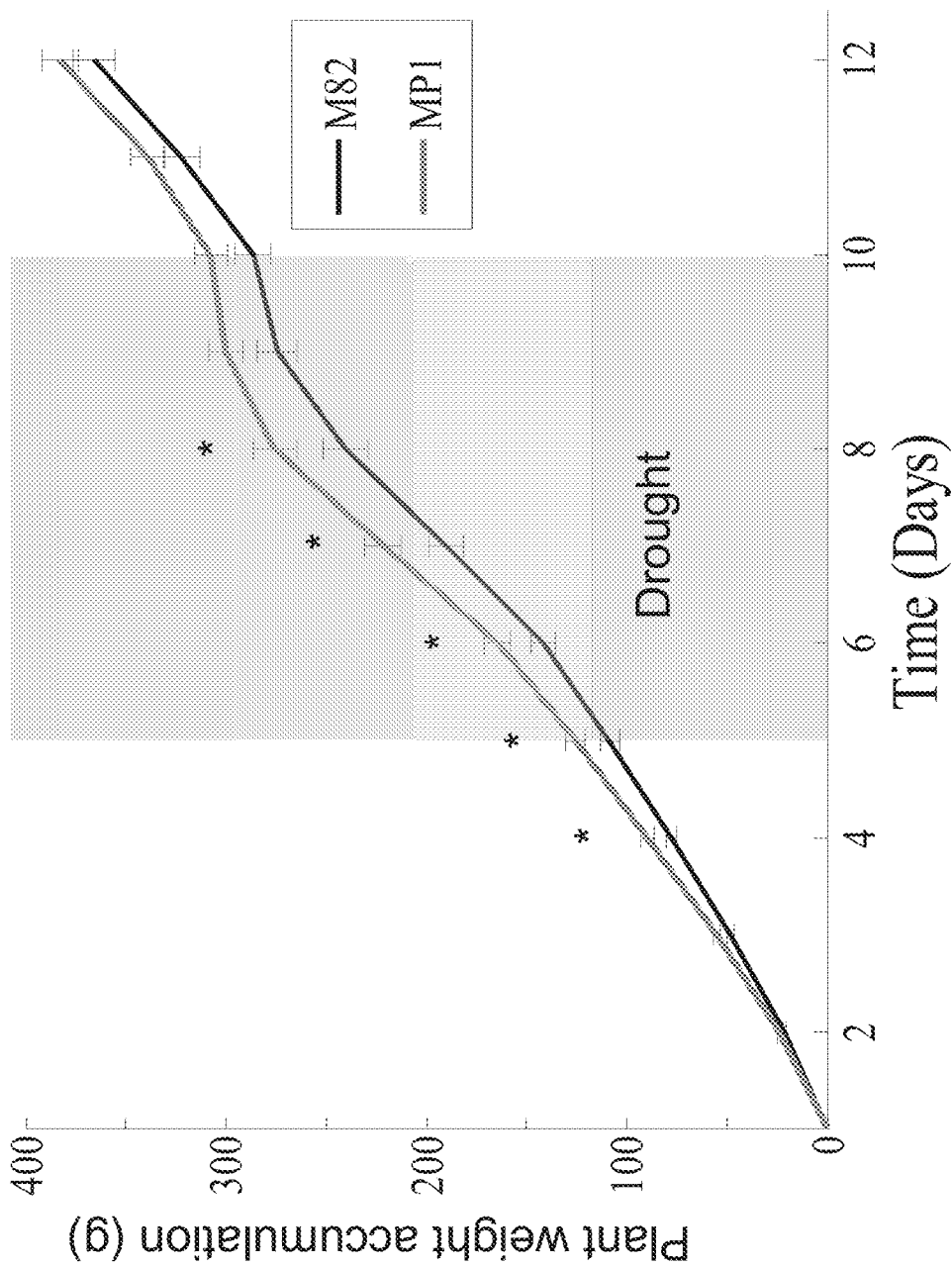
FIG. 24 shows whole-plant growth rate. Mean (±SE) of the whole-plant weight (g). Asterisks indicate a significant difference (Student's t-test, p<0.05) between the lines.

Several studies have revealed dynamic, valve-like behavior of $K_{leaf}$ (Cochard et al., 2007; Levin et al., 2007) and root radial conductance (Maggio and Joly, 1995; Carvajal et al., 1996; Clarkson et al., 2000; Tournaire-Roux et al., 2003; Gorska et al., 2008; Bramley et al., 2010) that is strongly dependent upon and responsive to ambient signals. This radial flux is likely regulated by aquaporins, both in the leaf and in the root (Tournaire-Roux et al., 2003; Maurel et al., 2009; Shatil-Cohen et al., 2011; Shatil-Cohen and Moshelion, 2012). We suggest that differential TIP and PIP expression plays a role in the osmotic-hydraulic regulation mechanism that differentiates isohydric from anisohydric behavior. Accordingly, greater hydraulic conductance (supporting greater water inflow) will counterbalance the higher E rates that are the result of higher $gs_c$. High levels of vacuolar osmotic permeability will provide hydraulic buffering, enabling osmotic homeostasis of the cytoplasm in the face of transient changes in the leaf supply-demand water balance. We suggest that greater osmotic buffering will lead to longer periods before a stress signal is initiated in the cytoplasm, resulting in stomata remaining open for longer periods, longer periods of photosynthesis and more rapid growth of the anisohydric line (FIG. 24). Yet, as soon as $\theta_{cr}$ is reached, this control strategy will lead to faster loss of RWC, more rapid leaf desiccation and greater risk of hydraulic failure.

Figures 19A, 19B:
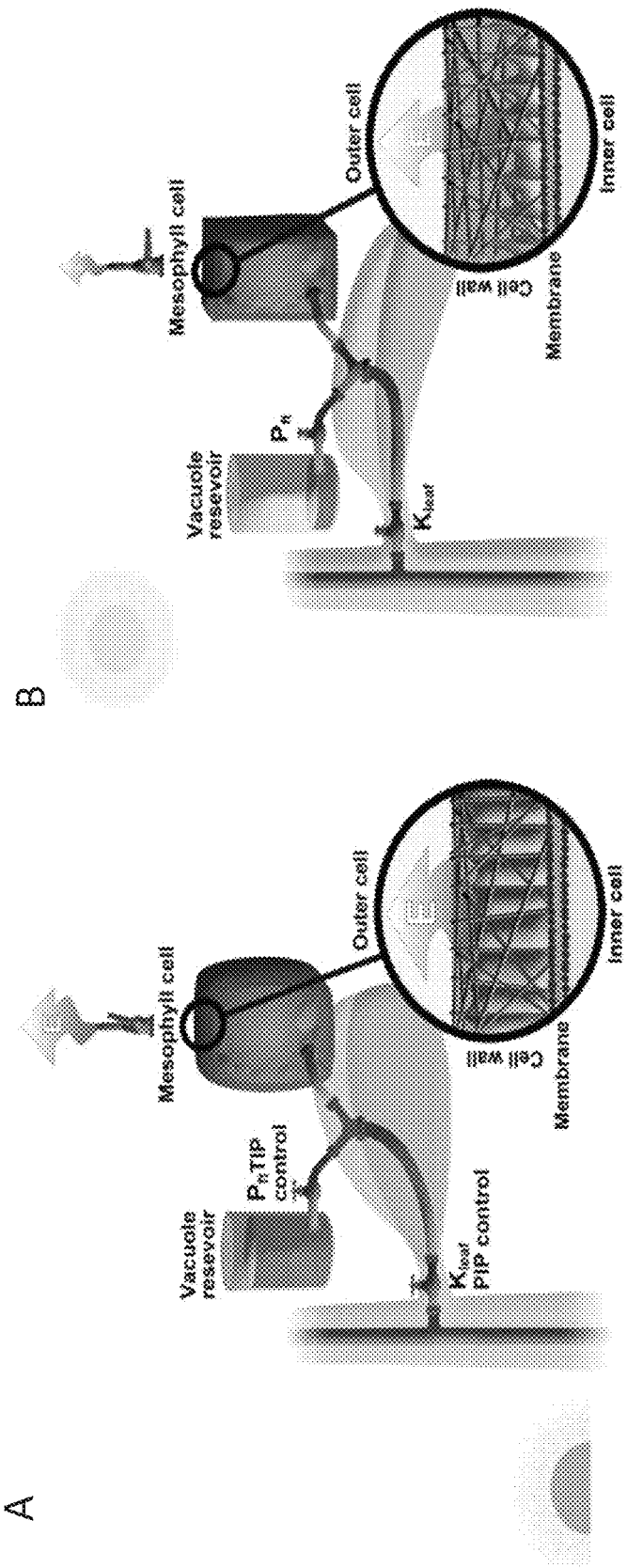
FIGS. 19A and 19B show vacuole water supply: The uninterrupted transpiration illustration. The dynamically buffered water-flow control of the leaf water status. (A) The leaf before dawn under conditions of high soil water availability and (B) the same leaf at midday under conditions of low soil water availability. The negative water potential in the leaf is generated within the microcapillary structure of the mesophyll cell walls (Nobel, 2009), in close proximity to the cell cytoplasm, which puts the cytoplasm at risk of dehydration. We propose that this risk is averted by (i) maintaining the low conductivity of the plasma membrane that separates these two compartments and (ii) the buffering effect of the vacuole based on the elevated water conductivity of the tonoplast ($P_{ft}$). In parallel, the decreasing water potential in the cell wall pulls in water from the xylem. In addition, the $K_{leaf}$ 'valve' (the bundle sheath water conductivity) controls the movement of water into the leaf (Shatil-Cohen et al., 2011; Shatil-Cohen and Moshelion, 2012; Pantin et al., 2013), in correlation with the leaf water potential, relative water content (RWC) and the rate of turgor loss. Higher $P_{ft}$ and $K_{leaf}$ levels due to prolonged activity of TIPs and PIPs, respectively, are believed to be part of the molecular mechanism responsible for the difference between anisohydric and isohydric plants.

The present example provides hydraulic analogy for the movement of water in SPAC (FIGS. 19A and 19B). The hydraulic analogy is based on dynamic radial hydraulic resistances that vary nonlinearly with potential and are putatively controlled by PIPs. The vacuole water reservoirs retain and release water via TIPs to compensate for cytoplasmic water deficits in the presence of a negative leaf water balance.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Ache P, Bauer H, Kollist H, Al-Rasheid K A S, Lautner S, Hartung W, Hedrich R (2010) Stomatal action directly feeds back on leaf turgor: new insights into the regulation of the plant water status from non-invasive pressure probe measurements. Plant Journal 62: 1072-1082.

Bartlett M K, Scoffoni C, Sack L (2012) The determinants of leaf turgor loss point and prediction of drought tolerance of species and biomes: a global meta-analysis. Ecology Letters 15: 393-405.

Birnbaum K, Shasha D E, Wang J Y, Jung J W, Lambert G M, Galbraith D W, Benfey P N (2003) A gene expression map of the Arabidopsis root. Science 302: 1956-1960.

Bramley H, Turner N C, Turner D W, Tyerman S D (2010) The contrasting influence of short-term hypoxia on the hydraulic properties of cells and roots of wheat and lupin. Functional Plant Biology 37: 183-193.

Buck A L (1981) New equations for computing vapor pressure and enhancement factor. Journal of Applied Meteorology 20: 1527-1532.

Buckley T N (2005) The control of stomata by water balance. New Phytologist 168: 275-292.

Carvajal M, Cooke D, Clarkson D (1996) Responses of wheat plants to nutrient deprivation may involve the regulation of water-channel function. Planta 199: 372-381.

Clarkson D T, Carvajal M, Henzler T, Waterhouse R N, Smyth A J, Cooke D T, Steudle E (2000) Root hydraulic conductance: diurnal aquaporin expression and the effects of nutrient stress. Journal of Experimental Botany 51: 61-70.

Cochard H, Venisse J-Sp, Barigah TtSvr, Brunel N, Herbette S p, Guilliot A s, Tyree M T, Sakr S (2007) Putative Role of Aquaporins in Variable Hydraulic Conductance of Leaves in Response to Light. Plant Physiology 143: 122-133.

Farquhar G D (1978) Feedforward Responses of Stomata to Humidity. Functional Plant Biology 5: 787-800.

Farquhar G D, Wong S C (1984) An Empirical Model of Stomatal Conductance. Functional Plant Biology 11: 191-210.

Feddes R A, Raats P A C (2004) Parameterizing the soil-water-plant root system. In RAdR Feddes, G. H.; Van Dam, J. C., ed, Unsaturated-zone Modeling: Progress, Challenges and Applications Kluwer Academic, Wageningen, pp 95-132.

Franks P J, Cowan I R, Farquhar G D (1997) The apparent feedforward response of stomata to air vapor pressure deficit: information revealed by different experimental procedures with two rainforest trees. Plant, Cell & Environment 20: 142-145.

Geisler M, Sack F D (2002) Variable timing of developmental progression in the stomatal pathway in *Arabidopsis cotyledons*. New Phytologist 153: 469.

Gorska A, Zwieniecka A, Michele Holbrook N, Zwieniecki M (2008) Nitrate induction of root hydraulic conductivity in maize is not correlated with aquaporin expression. Planta 228: 989-998.

Holloway-Phillips M-M, Brodribb T J (2011) Minimum hydraulic safety leads to maximum water-use efficiency in a forage grass. Plant, Cell & Environment 34: 302-313.

Kaldenhoff R, Bertl A, Otto B, Moshelion M, Uehlein N (2007) Characterization of Plant Aquaporins. 428: 505-531

Kramer P J, Boyer J S (1995) Water relations of plants and soils. Academic Press, Inc.

Levin M, Lemcoff J H, Cohen S, Kapulnik Y (2007) Low air humidity increases leaf-specific hydraulic conductance of *Arabidopsis thaliana* (L.) Heynh (Brassicaceae). Journal of Experimental Botany 58: 3711-3718.

Levin M, Lemcoff J H, Cohen S, Kapulnik Y (2007) Low air humidity increases leaf-specific hydraulic conductance of *Arabidopsis thaliana* (L.) Heynh (Brassicaceae). Journal Of Experimental Botany 58: 3711.

Lin W, Peng Y, Li G, Arora R, Tang Z, Su W, Cai W (2007) Isolation and functional characterization of PgTIP1, a hormone-autotrophic cells-specific tonoplast aquaporin in ginseng. Journal Of Experimental Botany 58: 947-956.

Maggio A, Joly R J (1995) Effects of Mercuric Chloride on the Hydraulic Conductivity of Tomato Root Systems (Evidence for a Channel-Mediated Water Pathway). Plant Physiology 109: 331-335.

Maurel C, Santoni V, Luu D-T, Wudick M M, Verdoucq L (2009) The cellular dynamics of plant aquaporin expression and functions. Current Opinion In Plant Biology 12: 690-698.

Maurel C, Simonneau T, Sutka M (2010) The significance of roots as hydraulic rheostats. Journal Of Experimental Botany 61: 3191-3198.

Maurel C, Verdoucq L, Luu D-T, Santoni V (2008) Plant Aquaporins: Membrane Channels with Multiple Integrated Functions. Annual Review Of Plant Biology 59: 595-624.

McDowell N, Pockman W T, Allen C D, Breshears D D, Cobb N, Kolb T, Plaut J, Sperry J, West A, Williams D G, Yepez E A (2008) Mechanisms of plant survival and mortality during drought: why do some plants survive while others succumb to drought? New Phytologist 178: 719-739.

McDowell N G (2011) Mechanisms Linking Drought, Hydraulics, Carbon Metabolism, and Vegetation Mortality. Plant Physiology 155: 1051-1059.

Monteith J L (1965) Evaporation and environment. Symposia of the Society for Experimental Biology 19: 205-234.

Mott K A, Franks P J (2001) The role of epidermal turgor in stomatal interactions following a local perturbation in humidity. Plant, Cell & Environment 24: 657-662.

Mott K A, Parkhurst D F (1991) Stomatal Responses To Humidity In Air And Helox. Plant Cell And Environment 14: 509.

Mott K A, Shope J C, Buckley T N (1999) Effects of humidity on light-induced stomatal opening: evidence for hydraulic coupling among stomata. Journal Of Experimental Botany 50: 1207-1213.

Nardini A, Raimondo F, Lo Gullo M A, Salleo S (2010) Leafminers help us understanding leaf hydraulic design. Plant, Cell & Environment.

Nobel P (2009) Physicochemical and Environmental Plant Physiology.

Pantin F, Monnet F, Jannaud D, Costa J M, Renaud J, Muller B, Simonneau T, Genty B (2013) The dual effect of abscisic acid on stomata. New Phytologist 197: 65-72.

Peng Y, Lin W, Cai W, Arora R (2007) Overexpression of a Panax ginseng tonoplast aquaporin alters salt tolerance, drought tolerance and cold acclimation ability in transgenic *Arabidopsis* plants. Planta 226: 729-740.

Pou A, Medrano H, Flexas J, Tyerman S D (2012) A putative role for TIP and PIP aquaporins in dynamics of leaf hydraulic and stomatal conductances in grapevine under water stress and re-watering. Plant, Cell & Environment: no-no.

Sack L, Holbrook N M (2006) Leaf hydraulics. Annual Review Of Plant Biology 57: 361.

Sack L, Holbrook N M (2006) Leaf hydraulics. Annual Review of Plant Biology 57: 361-381.

Sade D, Eybishtz A, Gorovits R, Sobol I, Czosnek H (2012) A developmentally regulated lipocalin-like gene is overexpressed in Tomato yellow leaf curl virus-resistant tomato plants upon virus inoculation, and its silencing abolishes resistance. Plant Mol Biol 80: 273-287.

Sade N, Gebremedhin A, Moshelion M (2012) Risk-taking plants: Anisohydric behavior as a stress-resistance trait. Plant Signaling & Behavior 7: 767-770.

Sade N, Gebretsadik M, Seligmann R, Schwartz A, Wallach R, Moshelion M (2010) The Role of Tobacco Aquaporin1 in Improving Water Use Efficiency, Hydraulic Conductivity, and Yield Production Under Salt Stress. Plant Physiology 152: 245-254.

Sade N, Vinocur B J, Diber A, Shatil A, Ronen G, Nissan H, Wallach R, Karchi H, Moshelion M (2009) Improving plant stress tolerance and yield production: is the tonoplast aquaporin SlTIP2;2 a key to isohydric to anisohydric conversion? New Phytol 181: 651-661.

Shatil-Cohen A, Attia Z, Moshelion M (2011) Bundle-sheath cell regulation of xylem-mesophyll water transport via aquaporins under drought stress: a target of xylem-borne ABA? The Plant Journal 67: 72-80.

Shatil-Cohen A, Moshelion M (2012) Smart pipes: The bundle sheath role as xylem-mesophyll barrier. Plant Signaling & Behavior 7: 1088-1091.

Shatil-Cohen A, Moshelion M (2012) Smart Pipes: The bundle sheath role as xylem-mesophyll barrier. Plant Signaling & Behavior 7: 1088-1091.

Steudle E (2000) Water uptake by roots: effects of water deficit. J. Exp. Bot. 51: 1531-1542.

Taiz L, Zeiger E (2002) Plant physiology, Ed 3rd. Sinauer Associates, Sunderland, Mass.

Tardieu F, Simonneau T (1998) Variability among species of stomatal control under fluctuating soil water status and evaporative demand: modelling isohydric and anisohydric behaviours. Journal Of Experimental Botany 49: 419-432.

Topp G C, Davis J L, Annan A P (1980) Electromagnetic determination of soil water content: Measurements in coaxial transmission lines. Water Resour. Res. 16: 574-582.

Tournaire-Roux C, Sutka M, Javot H, Gout E, Gerbeau P, Luu D-T, Bligny R, Maurel C (2003) Cytosolic pH regulates root water transport during anoxic stress through gating of aquaporins. Nature 425: 393-397.

Tyerman S D, Bohnert H J, Maurel C, Steudle E, Smith J A C (1999) Plant aquaporins: their molecular biology, biophysics and significance for plant water relations. Journal of Experimental Botany 50: 1055-1071.

Tyerman S D, Niemietz C M, Bramley H (2002) Plant aquaporins: multifunctional water and solute channels with expanding roles. Plant Cell Environ 25: 173-194.

Uehlein N, Lovisolo C, Siefritz F, Kaldenhoff R (2003) The tobacco aquaporin NtAQP1 is a membrane $CO_2$ pore with physiological functions. Nature 425: 734-737

Van-Genuchten M T (1980) A Closed-form Equation for Predicting the Hydraulic Conductivity of Unsaturated Soils. Soil Sci. Soc. Am. J. 44:892-898.

Wallach R, Da-Costa N, Raviv M, Moshelion M (2010) Development of synchronized, autonomous, and self-regulated oscillations in transpiration rate of a whole tomato plant under water stress. J. Exp. Bot. 61: 3439-3449.

What is claimed is:

1. A system for characterizing a plant, the system comprising:
a plurality of sensors configured to generate signals indicative of a transpiration rate from the whole plant and a water uptake rate into the whole plant, wherein said signals indicative of said transpiration rate comprise at least one signal selected from the group consisting of a signal indicative of a weight gain of the plant and a signal indicative of a cooling rate of the plant; and
a processor having a circuit configured to: (i) receive said signals from said sensors, (ii) process said signals to calculate a first parameter indicative of said transpiration rate and a second parameter indicative of said water uptake rate, and (iii) classify said plant into at least one classification group according to said calculated parameters, wherein said circuit of said processor is configured for calculating at least one of said first parameter and said second parameters at least once every 60 minutes.

2. The system of claim 1, wherein said circuit of said processor is further configured for calculating both said first parameter and said second parameter at least once every 60 minutes.

3. The system according to claim 1, wherein said circuit of said processor is further configured to calculate a score based on said calculated parameters.

4. The system according to claim 3, wherein said plant is a member of a population of plants, and the processor is configured to calculate said score for each plant in the population and to rank the plants of the population based on said score.

5. The system according to any of claim 1, wherein said sensors comprise a weight sensor for sensing said first parameter and a soil water content sensor for sensing said second parameter.

6. The system according to claim 5, wherein said soil water content sensor is placed in the vicinity of a root of said plant.

7. The system according to claim 5, further comprising a container containing soil and water and configured to receive the plant, wherein said weight sensor is a load cell arranged to sense a weight or a change in weight of said container and contents thereof.

8. The system according to claim 5, further comprising a cover on said container to reduce or prevent evaporation of the water from the container.

9. The system according to claim 5, wherein said circuit of said processor is further configured to calculate said water uptake rate from a time-dependent signal generated by said soil water content sensor, thereby to provide a time-dependence of said water uptake rate.

10. The system according to claim 9, wherein said circuit of said processor is further configured to calculate a rate of change of said water uptake rate from said time-dependence of said water uptake rate.

11. The system according to claim 1, wherein said circuit of said processor is further configured to calculate a water usage efficiency of the plant.

12. The system according to claim 1, wherein said circuit of said processor is further configured to calculate said transpiration rate and to normalize said calculated transpiration rate to at least one normalizing quantity selected from the group consisting of a surface area of the leaves of said plant, a density of stomata in the leaves and an amount of soil water.

13. The system according to claim 1, wherein said classification group is one of: (i) a classification group of plants exhibiting isohydric behavior and (ii) a classification group of plants exhibiting anisohydric behavior.

14. The system according to of claim 13, wherein said circuit of said processor is further configured to calculate variability in leaf relative water content, and wherein said classification is according to said variability.

15. The system according to claim 14, wherein said circuit of said processor is further configured to calculate a shoot weight ratio and a root uptake rate, and wherein said variability is calculated based on a difference between said shoot weight ratio and said root uptake rate.

16. The system according to claim 14, wherein said circuit of said processor is further configured to receive expression profiles of at least one aquaporin and wherein said classification is based, in part, on said received expression profile.

17. The system according to claim 13, wherein said circuit of said processor is further configured to estimate a whole plant hydraulic conductivity based on at least one of said parameters, and wherein said classification is based, at least in part on said plant hydraulic conductivity.

18. A method of characterizing a plant, the method comprising:
receiving from a plurality of sensors signals indicative of a transpiration rate from the whole plant and a water uptake rate into the whole plant, wherein said signals indicative of said transpiration rate comprise at least one signal selected from the group consisting of a signal indicative of a weight gain of the plant and a signal indicative of a cooling rate of the plant, and
processing said signals to calculate from said signals a first parameter indicative of said transpiration rate and a second parameter indicative of said water uptake rate and to characterize the plant according to said calculated parameters, wherein at least one of said first parameter and said second parameter is calculated at least once every 60 minutes;
wherein said plant is in a container containing soil, water and a wick partially submerged in said water, and wherein the method comprises measuring an evaporation rate from said wick, and comparing said calculated first parameter with said evaporation rate.

19. A method of characterizing a plant, the method comprising:
receiving from a plurality of sensors signals indicative of a transpiration rate from the whole plant and a water uptake rate into the whole plant, wherein said signals indicative of said transpiration rate comprise at least one signal selected from the group consisting of a signal indicative of a weight gain of the plant and a signal indicative of a cooling rate of the plant, and
processing said signals to calculate from said signals a first parameter indicative of said transpiration rate and a second parameter indicative of said water uptake rate, and to classify said plant into at least one classification group according to said calculated parameters.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
ggaaaagctt gcctatgtgg                                              20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
cctgcagctt ccataccaat                                              20

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
gggttctggt atggctttca                                              20

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
tgtttccacc aacaaaagca                                              20

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 5
atggctggcg gcgtagctat t                                            21

<210> SEQ ID NO 6
<211> LENGTH: 20
<212> TYPE: DNA
<213> ORGANISM: Artificial sequence
```

```
<220> FEATURE:
<223> OTHER INFORMATION: Single strand DNA oligonucleotide

<400> SEQUENCE: 6
agagcaaatc catggcaaac                                              20

<210> SEQ ID NO 7
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 7
agtaagaaac aataatgcca atttc                                        25

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
aaaagaactc agctgttgca g                                            21

<210> SEQ ID NO 9
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 9
gctcatgatg aagctccagt t                                            21

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
ggcctcttaa gaaagcaaac aa                                           22

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
gtgaagggct tcatggtagg                                              20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
ggaagtggtg ccaaaatagg                                              20
```

```
<210> SEQ ID NO 13
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 13
ggtctcatgt tcctcttcca a                                             21

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
catgaccaaa cggggtagtt                                               20

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
ctatgaaccc agcacgatca                                               20

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
ctgaggttgg aagtggtgtg                                               20

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
gggtggtggt gctaatgaac                                               20

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
ttggaagtgg tgccaataca                                               20
```